US012691303B2

(12) United States Patent
Ren et al.

(10) Patent No.: US 12,691,303 B2
(45) Date of Patent: Jul. 28, 2026

(54) TECHNIQUES FOR DETECTING IN REAL-TIME PROTON BEAM THERAPY THREE DIMENSIONAL DOSE DELIVERED

(71) Applicants: University of Maryland, Baltimore, Baltimore, MD (US); Duke University, Durham, NC (US); The Regents of the University of California, Oakland, CA (US)

(72) Inventors: Lei Ren, Clarksville, MD (US); Zhuoran Jiang, Durham, NC (US); Leshan Sun, Irvine, CA (US); Liangzhong Xiang, Irvine, CA (US)

(73) Assignees: University of Maryland, Baltimore, MD (US); Duke University, Durham, NC (US); Regents of the University of California, Oakland, CA (US)

( * ) Notice: Subject to any disclaimer, the term of this patent is extended or adjusted under 35 U.S.C. 154(b) by 171 days.

(21) Appl. No.: 18/764,627

(22) Filed: Jul. 5, 2024

(65) Prior Publication Data

US 2025/0010103 A1     Jan. 9, 2025

Related U.S. Application Data

(60) Provisional application No. 63/525,295, filed on Jul. 6, 2023.

(51) Int. Cl.
*A61N 5/10* (2006.01)
*G16H 20/40* (2018.01)
(52) U.S. Cl.
CPC .......... *A61N 5/1049* (2013.01); *G16H 20/40* (2018.01); *A61N 2005/1058* (2013.01); *A61N 2005/1087* (2013.01)

(58) Field of Classification Search
CPC .......... A61N 5/1049; A61N 2005/1058; A61N 2005/1087; G16H 20/40
See application file for complete search history.

(56) References Cited

U.S. PATENT DOCUMENTS

| | | | |
|---|---|---|---|
| 4,385,634 A † | 5/1983 | Bowen | |
| 9,545,527 B2 † | 1/2017 | Moskvin | |
| 9,789,339 B2 † | 10/2017 | Moskvin | |

FOREIGN PATENT DOCUMENTS

| | | | | |
|---|---|---|---|---|
| CN | 112023279 | † 12/2020 | | |
| CN | 115137996 A | * 10/2022 | .......... | A61N 5/1075 |

OTHER PUBLICATIONS

Schauer et al., "Proton beam range verification by means of iono-acoustic measurements at clinically relevant doses using a correlation-based evaluation", Frontiers in Oncology, DOI:10.3389/fonc.2022.925542, 18 pages. (Year: 2022).*

(Continued)

*Primary Examiner* — Kiho Kim
(74) *Attorney, Agent, or Firm* — Wolter Van Dyke Davis, PLLC; Eugene Molinelli; Cian O'Brien

(57) ABSTRACT

Techniques for detecting real-time proton beam dose include retrieving conversion data for converting proton dose to acoustic pressure based on medical imagery. 3D medical imagery is retrieved of a first region of interest (ROI) inside a first subject. A real-time signal indicates ultrasound pressure at a 2D ultrasound array disposed outside and in contact with the first subject close to the first ROI. Real-time 3D dose delivered in the first ROI is determined by inputting the real-time signal into a dose detection module that includes a neural network. The neural network is trained on multiple instances of a training set. Each instance includes: simulated proton dose delivered to a similar ROI inside a second subject; simulated pressure generation from that simulated dose based on the conversion data and a similar 3D medical (Continued)

ITERATIVE TRAINING PROCESSS
(many well known methods
for adjusting
parameter values)

image; and simulated acoustic transmission from the similar ROI to a similar two-dimensional ultrasound transducer array similarly disposed.

20 Claims, 16 Drawing Sheets

(56) References Cited

OTHER PUBLICATIONS

Ahmad, M., et al., "Theoretical detection threshold of the proton-acoustic range verification technique.", Medical physics, vol. 42, No. 10, Oct. 2015, pp. 5735-5744.

Assmann, W., et al., "Ionoacoustic characterization of the proton Bragg peak with submillimeter accuracy.", Medical physics, vol. 42, No. 2, Feb. 2015, pp. 567-574.

Chen, H., et al., "Learn: Learned experts assessment-based reconstruction network for sparse-data CT.", IEEE transactions on medical imaging, vol. 37, No. 6, Jun. 2018, pp. 1333-1347.

Cheng, A., et al., "Deep learning image reconstruction method for limited-angle ultrasound tomography in prostate cancer.", Medical Imaging 2019: Ultrasonic Imaging and Tomography, vol. 10955, 2019, 8 pages.

Forghani, F., et al., "Simulation of x-ray-induced acoustic imaging for absolute dosimetry: Accuracy of image reconstruction methods.", Medical physics, vol. 47, No. 3, Mar. 2020, pp. 1280-1290.

Freijo, C., et al., "Dictionary-based protoacoustic dose map imaging for proton range verification.", Photoacoustics, vol. 21, Jan. 13, 2021, 11 pages.

Hickling, S., et al., "Ionizing radiation-induced acoustics for radiotherapy and diagnostic radiology applications.", Medical physics, vol. 45, No. 7, Jul. 2018, pp. e707-e721.

Hristova, Y., et al., "Reconstruction and time reversal in thermoacoustic tomography in acoustically homogeneous and inhomogeneous media.", Inverse problems, vol. 24, No. 5, 2008, 28 pages.

Huang, Y., et al., "Data consistent artifact reduction for limited angle tomography with deep learning prior.", International workshop on machine learning for medical image reconstruction, 2019, 12 pages.

Jiang, Z., et al., "A multi-scale framework with unsupervised joint training of convolutional neural networks for pulmonary deformable image registration.", Physics in Medicine & Biology, vol. 65, No. 1, 2020, 23 pages.

Jiang, Z., et al., "Augmentation of CBCT reconstructed from under-sampled projections using deep learning.", IEEE transactions on medical imaging, vol. 38, No. 11, Nov. 2019, pp. 2705-2715.

Jiang, Z., et al., "Enhancing digital tomosynthesis (DTS) for lung radiotherapy guidance using patient-specific deep learning model.", Physics in Medicine & Biology, vol. 66, No. 3, 2021, 22 pages.

Jiang, Z., et al., "Prior image-guided cone-beam computed tomography augmentation from under-sampled projections using a convolutional neural network.", Quantitative imaging in medicine and surgery, vol. 11, No. 12, 2021, pp. 4767-4780.

Jones, K. C., et al., "Acoustic-based proton range verification in heterogeneous tissue: simulation studies.", Physics in Medicine & Biology, vol. 63, No. 2, 2018, 29 pages.

Jones, K. C., et al., "Experimental observation of acoustic emissions generated by a pulsed proton beam from a hospital-based clinical cyclotron.", Medical physics, vol. 42, No. 12, Dec. 2015, pp. 7090-7097.

Kingma, D. P., "Adam: A method for stochastic optimization.", arXiv preprint, 2014, 13 pages.

Lascaud, J., et al., "Investigating the accuracy of co-registered ionoacoustic and ultrasound images in pulsed proton beams.", Physics in Medicine & Biology, vol. 66, No. 18, 2021, 13 pages.

Litjens, G., et al., "A survey on deep learning in medical image analysis.", Medical image analysis, vol. 42, 2017, pp. 60-88.

Maier, A., et al., "A gentle introduction to deep learning in medical image processing.", Z. Med. Phy., vol. 29, No. 2, 2019, pp. 86-101.

Ronneberger, O., et al., "U-net: Convolutional networks for biomedical image segmentation.", Medical image computing and computer-assisted intervention, Oct. 5-9, 2015, part III 18, 8 pages.

Schlemper, J., et al., "A deep cascade of convolutional neural networks for dynamic MR image reconstruction.", IEEE transactions on Medical Imaging, vol. 37, No. 2, 2017, pp. 491-503.

Tajbakhsh, N., et al., "Embracing imperfect datasets: A review of deep learning solutions for medical image segmentation.", Medical image analysis, vol. 63, 2020, 30 pages.

Treeby, B. E., et al., "k-Wave: MATLAB toolbox for the simulation and reconstruction of photoacoustic wave fields.", Journal of biomedical optics, vol. 15, No. 2, Mar. 2010, 12 pages.

Wang, M., et al., "Toward in vivo dosimetry for prostate radiotherapy with a transperineal ultrasound array: a simulation study.", IEEE transactions on radiation and plasma medical sciences, vol. 5, No. 3, 2020, pp. 373-382.

Xu, M., et al., "Universal back-projection algorithm for photoacoustic computed tomography.", Physical Review E-Statistical, vol. 71, No. 1, 2005, 7 pages.

Yang, Y., et al., "Two-stage selective ensemble of CNN via deep tree training for medical image classification.", IEEE Transactions on Cybernetics, vol. 52, No. 9, Sep. 2021, pp. 9194-9207.

Yao, D.-K., et al., "Photoacoustic measurement of the Grüneisen parameter of tissue.", Journal of biomedical optics, vol. 19, No. 1, Jan. 2014, 8 pages.

Yao, S., et al., "Feasibility study of range verification based on proton-induced acoustic signals and recurrent neural network.", Physics in Medicine & Biology, vol. 65, No. 21, 2020, 15 pages.

Yao, S., et al., "Further investigation of 3D dose verification in proton therapy utilizing acoustic signal, wavelet decomposition and machine learning.", Biomedical physics & engineering express, vol. 8, No. 1, 2022, 16 pages.

Yu, J., et al., "Design of a volumetric imaging sequence using a vantage-256 ultrasound research platform multiplexed with a 1024-element fully sampled matrix array.", IEEE transactions on ultrasonics, ferroelectrics, and frequency control, vol. 67, No. 2, Feb. 2019, pp. 248-257.

Yu, Y., et al., "Simulation studies of time reversal-based protoacoustic reconstruction for range and dose verification in proton therapy.", Medical physics, vol. 46, No. 8, Aug. 2019, pp. 3649-3662.

Zhang, H.-M., et al., "A review on deep learning in medical image reconstruction.", Journal of the Operations Research Society of China, vol. 8, No. 2, Oct. 4, 2022, pp. 311-340.

Zhuoran Jiang, Siqi Wang, Yifei Xu, Leshan Sun, Gilberto Gonzalez, Yong Chen, Q. Jackie Wu, Liangzhong Xiang, Lei Ren. "Radiation-induced Acoustic Signal Denoising using a Supervised Deep Learning Framework for Imaging and Therapy Monitoring," [Submitted on Apr. 26, 2023]. arXiv:2304.13868 (or arXiv:2304.13868v1) https://doi.org/10.48550/arXiv.2304.13868.†

Zhuoran Jiang, Leshan Sun, Weiguang Yao, Q. Jackie Wu, Liangzhong Xiang, Lei Ren, "3D In Vivo Dose Verification in Prostate Proton Therapy with Deep Learning-based Proton-acoustic Imaging," Phys Med Bio 67(21).†

Yu Y, Li Z, Zhang D, Xing L, Peng H. Simulation studies of time reversal-based protoacoustic reconstruction for range and dose verification in proton therapy. Medical physics. 2019; 46(8): 3649-3662.†

Yu Y, Qi P, Peng H. Feasibility study of 3D time-reversal reconstruction of proton-induced acoustic signals for dose verification in the head and the liver: A simulation study. Med Phys. Aug. 2021;48(8):4485-4497. doi: 10.1002/mp.15046. Epub Jul. 12, 2021. PMID: 34120348.†

Zhang, Oraiqat, Litzenberg, Chang, Hadley, Sunbul, Matuszak, Tichacek, Moros, Carson, Cuneo, Wang, El Naqa. (published Jan. 2, 2023), Nature Biotechnology 41(8):1160-1167.†

Patch, et al., "Thermoacoustic range verification during pencil beam delivery of a clinical plan to an abdominal imaging phantom," (2021), Radiotherapy and Oncology, 159, pp. 224-230.†

Li Z, Wang Y, Yu Y, Fan K, Xing L, Peng H. Technical Note: Machine learning approaches for range and dose verification in proton therapy using proton-induced positron emitters. Med Phys. Dec. 2019;46(12):5748-5757. doi: 10.1002/mp.13827. Epub Oct. 10, 2019.PMID: 31529506.†

(56)        References Cited

OTHER PUBLICATIONS

Tseng, H.H., Luo, Y., Cui, S., Chien, J.T., Ten Haken, R.K., & El Naqa, I. "Deep reinforcement learning for automated radiation adaptation in lung cancer," (2017), Med. Phys. 44(12):6690-6705.†
Yao S, Hu Z, Zhang X, Lou E, Liang Z, Wang Y, Peng H. Feasibility study of range verification based on proton-induced acoustic signals and recurrent neural network. Phys Med Biol. Nov. 5, 2020;65(21):215017. doi: 10.1088/1361-6560/abaa5e.PMID: 32726760.†

* cited by examiner
† cited by third party

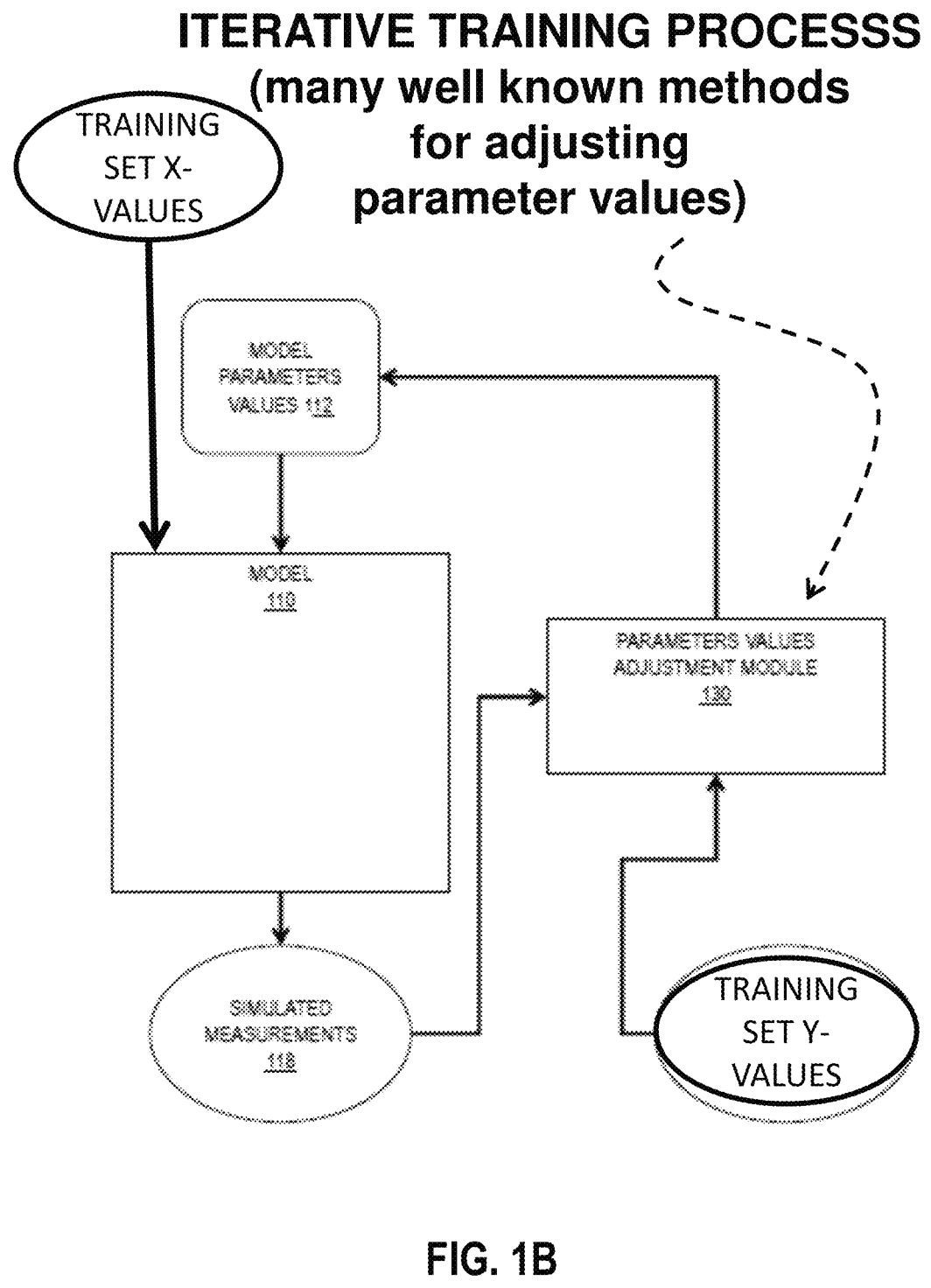

ITERATIVE TRAINING PROCESSS
(many well known methods for adjusting parameter values)

TRAINING SET X-VALUES

MODEL PARAMETERS VALUES 112

MODEL 110

PARAMETERS VALUES ADJUSTMENT MODULE 130

SIMULATED MEASUREMENTS 116

TRAINING SET Y-VALUES

FIG. 1B

RECTIFIED LINEAR UNITS
(ReLU)

TRAINING SET
INSTANCE
FORMATION 303

SINGLE OR AVERAGE
OR RANDOMIZED
PATIENT
REGION OF INTEREST
MEDICAL SCAN
3D VOXEL ARRAY  330

REGION OF INTEREST
EXPOSURE TO DOSE
TO PRESSURE
PARAMETERS
3D VOXEL ARRAY  331

REGION OF INTEREST
WITH SIMULATED PROTON BEAM
EXPOSURE IN 3D VOXEL ARRAY 332
(= GROUND TRUTH DOSE = Y2)

REGION OF INTEREST
WITH SIMULATED PRESSURE 334
(=GROUND TRUTH PRESSURE=Y1=X2)

REGION OF INTEREST
WITH SIMULATED ULTRASOUND ACOUSTIC
PROPAGATION CAUSED 336

SIMULTAED ULTRASOUND ARRIVAL TIME SERIES
AT 2D ULTRASOUND ARRAY PLUS RANDOM
RANGE EROOR AND MEASUREMENT NOISE
338 ( = X1)

FIG. 3C

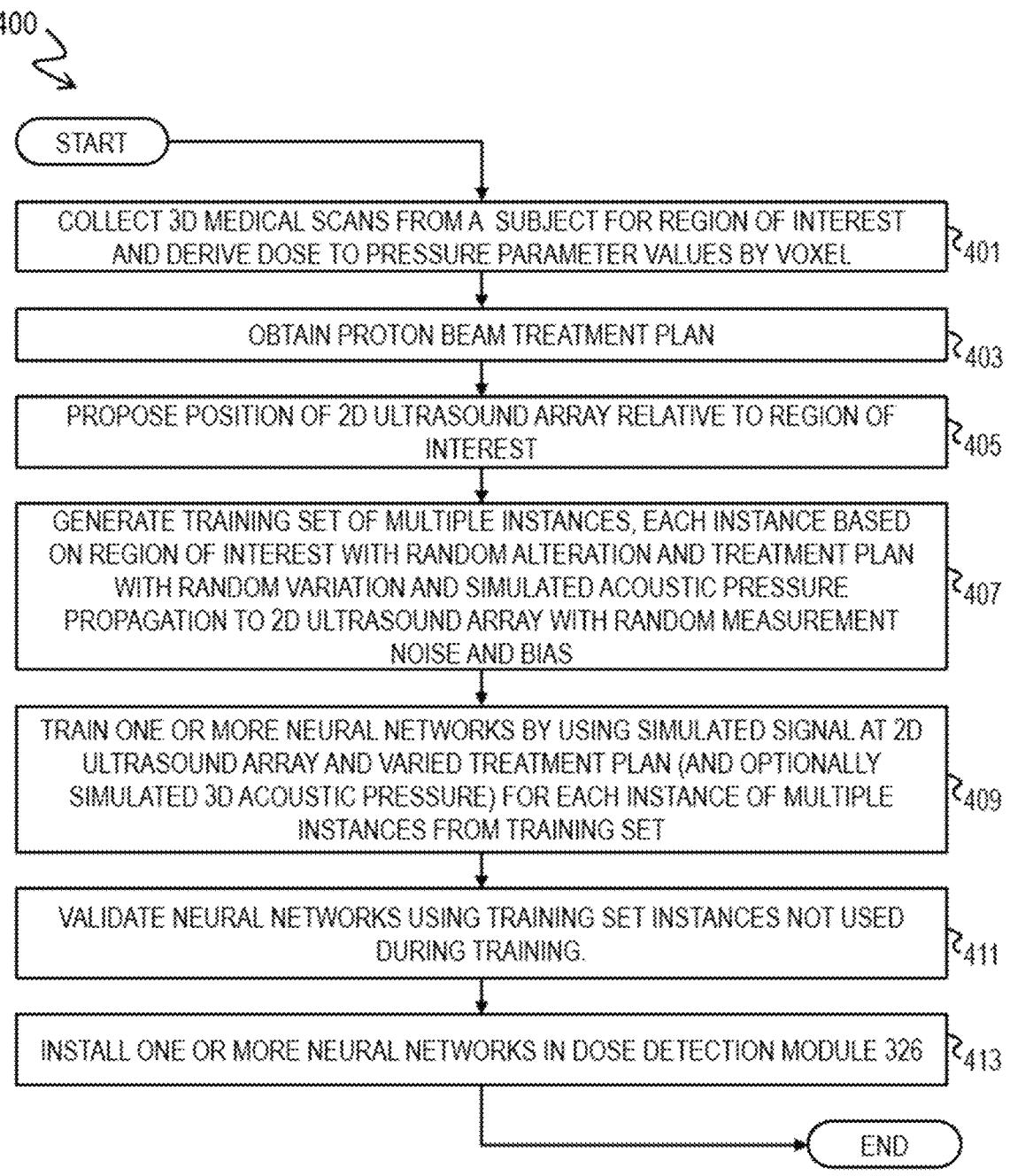

400

START

COLLECT 3D MEDICAL SCANS FROM A SUBJECT FOR REGION OF INTEREST AND DERIVE DOSE TO PRESSURE PARAMETER VALUES BY VOXEL — 401

OBTAIN PROTON BEAM TREATMENT PLAN — 403

PROPOSE POSITION OF 2D ULTRASOUND ARRAY RELATIVE TO REGION OF INTEREST — 405

GENERATE TRAINING SET OF MULTIPLE INSTANCES, EACH INSTANCE BASED ON REGION OF INTEREST WITH RANDOM ALTERATION AND TREATMENT PLAN WITH RANDOM VARIATION AND SIMULATED ACOUSTIC PRESSURE PROPAGATION TO 2D ULTRASOUND ARRAY WITH RANDOM MEASUREMENT NOISE AND BIAS — 407

TRAIN ONE OR MORE NEURAL NETWORKS BY USING SIMULATED SIGNAL AT 2D ULTRASOUND ARRAY AND VARIED TREATMENT PLAN (AND OPTIONALLY SIMULATED 3D ACOUSTIC PRESSURE) FOR EACH INSTANCE OF MULTIPLE INSTANCES FROM TRAINING SET — 409

VALIDATE NEURAL NETWORKS USING TRAINING SET INSTANCES NOT USED DURING TRAINING. — 411

INSTALL ONE OR MORE NEURAL NETWORKS IN DOSE DETECTION MODULE 326 — 413

END

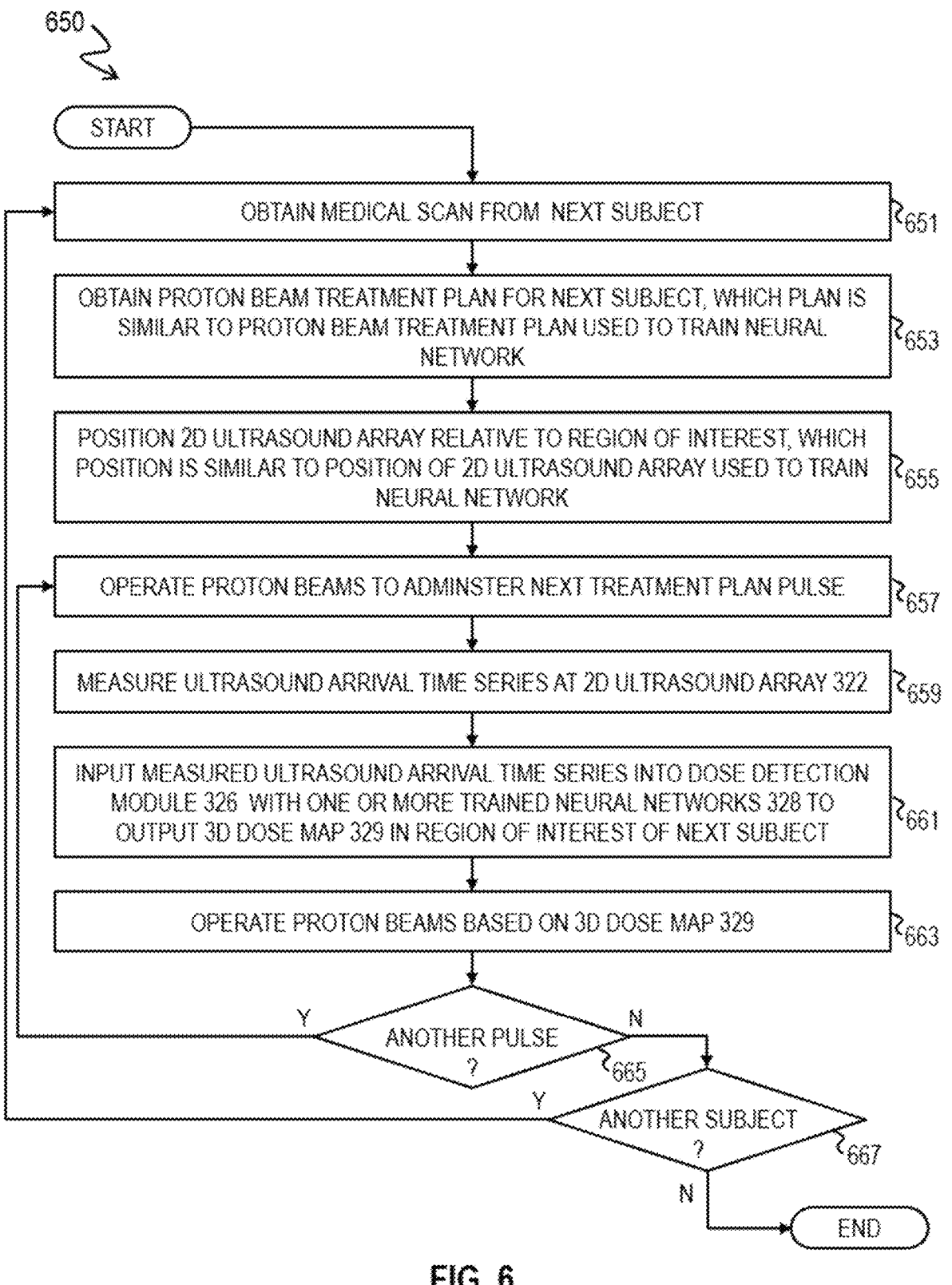

START

OBTAIN MEDICAL SCAN FROM NEXT SUBJECT 651

OBTAIN PROTON BEAM TREATMENT PLAN FOR NEXT SUBJECT, WHICH PLAN IS SIMILAR TO PROTON BEAM TREATMENT PLAN USED TO TRAIN NEURAL NETWORK 653

POSITION 2D ULTRASOUND ARRAY RELATIVE TO REGION OF INTEREST, WHICH POSITION IS SIMILAR TO POSITION OF 2D ULTRASOUND ARRAY USED TO TRAIN NEURAL NETWORK 655

OPERATE PROTON BEAMS TO ADMINSTER NEXT TREATMENT PLAN PULSE 657

MEASURE ULTRASOUND ARRIVAL TIME SERIES AT 2D ULTRASOUND ARRAY 322 659

INPUT MEASURED ULTRASOUND ARRIVAL TIME SERIES INTO DOSE DETECTION MODULE 326 WITH ONE OR MORE TRAINED NEURAL NETWORKS 328 TO OUTPUT 3D DOSE MAP 329 IN REGION OF INTEREST OF NEXT SUBJECT 661

OPERATE PROTON BEAMS BASED ON 3D DOSE MAP 329 663

Y   ANOTHER PULSE ? 665   N

Y   ANOTHER SUBJECT ? 667

N

END

FIG. 6

Table. 1. HU values and thermoacoustic parameters of different tissues.

| Tissue | HU value | v (m/s)$^{*}$ | $\rho$ (kg/m$^3$)$^{+}$ | $\Gamma^{\wedge}$ | $\rho \times \Gamma$ (kg/m$^3$) | $\alpha$ (dB/cm/MHz)$^{\#}$ |
|--------|----------|---------------|--------------------------|---------|----------------------------------|------------------------------|
| Air | [-1000, -200) | - | - | - | - | - |
| Water | air overwritten | 1500 | 1000 | 0.11 | 110 | 0.0022 |
| Fat | [-200, -50) | 1480 | 920 | 0.80 | 736 | 0.5 |
| Soft tissue | [-50, 100) | 1540 | 1040 | 0.30 | 312 | 1 |
| Bone | [100, max) | 2000 | 1900 | 0.80 | 1520 | 10 |

$^{*}$ Speed of sound. $^{+}$ Tissue density. $^{\wedge}$ Grüneisen parameter. $^{\#}$ Attenuation coefficient.

FIG. 7

Table. 2. Quantitative analysis of the pressure and dose maps. Metric values are calculated from all 26 testing cases.

| Modality | Metric | Value * |
|---|---|---|
| Pressure | RMSE | 0.061 ± 0.009 |
| Dose | RMSE | 0.044 ± 0.013 |
| | 90% isodose line Dice | 0.922 ± 0.024 |
| | 75% isodose line Dice | 0.934 ± 0.021 |
| | 50% isodose line Dice | 0.942 ± 0.017 |
| | 25% isodose line Dice | 0.966 ± 0.009 |
| | 10% isodose line Dice | 0.969 ± 0.009 |
| | Gamma index (3%/3mm) | 93.71% ± 3.34% |
| | Gamma index (2%/3mm) | 92.02% ± 3.94% |
| | Gamma index (3%/5mm) | 97.45% ± 2.23% |
| | Gamma index (2%/5mm) | 96.60% ± 2.64% |

Intensities of pressure and dose maps are normalized to [0, 1] to calculate the metrics.

* Numbers in the table are expressed as mean±standard deviation.

FIG. 8B

TECHNIQUES FOR DETECTING IN REAL-TIME PROTON BEAM THERAPY THREE DIMENSIONAL DOSE DELIVERED

CROSS-REFERENCE TO RELATED APPLICATIONS

This application claims benefit of Provisional Appln. 63/525,295, filed Jul. 6, 2023, the entire contents of which are hereby incorporated by reference as if fully set forth herein, under 35 U.S.C. § 119(e).

STATEMENT OF GOVERNMENTAL INTEREST

This invention was made with government support under Contract No. EB028324 awarded by National Institutes of Health. The government has certain rights in the invention.

BACKGROUND

During proton-beam therapy, protons deposit most of their energy at the end of the travel path, generating a 'Bragg Peak' in dose deposition and a fast dose drop-off beyond the peak. This characteristic allows proton therapy to potentially achieve significant healthy tissue sparing beyond the Bragg Peak with the dose concentrated to the target. However, proton therapy is highly susceptible to the delivery errors caused by patient positioning variations and anatomy motions/changes, as well as the systematic errors caused by range uncertainties in dose calculation. The sharp dose fall-off makes proton therapy much more sensitive to these errors than photon therapy, as a small delivery error can cause a significant underdose to the tumor or overdose to healthy tissues. Therefore, it's important to verify the dose delivery of proton therapy so that treatment errors can be detected and corrected to minimize their impact.

Dose delivery uncertainty is a major concern in proton therapy, adversely affecting the treatment precision and outcome. Recently, a promising technique, proton-acoustic (PA) imaging, has been developed to provide real-time in-vivo 3D dose verification. However, its dosimetry accuracy is limited due to the limited-angle view of the ultrasound transducer.

To address this urgent clinical need, various in vivo dose verification techniques have been proposed to estimate the deposited dose. These techniques can be divided into direct and indirect methods based on the measured signals.

Direct methods verify the proton range by directly measuring the dose or fluence. For example, implantable dosimeters/markers with wireless reading [1-3] have been investigated for range verification in proton therapy. These methods only provide limited point dose measurement without 3D volumetric information for dose verification, which is crucial for verifying the tumor and organ at risk (OAR) dose in proton therapy. Besides, these methods require the implantation of dosimeters, which is invasive. Proton radiology [4-6] is also developed to measure the proton beam range directly by delivering and imaging separate proton beams instead of treatment beams. These methods have limited image resolution, and more importantly, they don't verify the range of the actual treatment beams, thus not capable of verifying the actual delivered dose during treatment.

Indirect methods verify proton range by measuring the surrogate signals induced by the proton irradiation. Positron emission tomography (PET) [7-10] and prompt gamma (PG) imaging [11-15] have been developed to detect the gammas emitted from the positron emitters or excited nuclei generated along the proton beam path during treatment for range verification. Although annihilation gamma signal is initially correlated to dose deposition, the correlation of the resulting PET images to the delivered dose is severely degraded by biological washout and low signal intensity [16]. PG imaging is still under investigation with challenges of the degradation of PG data caused by false events and mis-ordering, and lack of true 3D information in the PG images [17,18]. Magnetic resonance imaging (MRI) [19,20] is also utilized to detect the tissue constitution changes caused by radiation. However, the MRI device is expensive and not available in the proton therapy room, and therefore it cannot provide in vivo range verification during the treatment delivery.

Recently, acoustic imaging has been investigated to detect proton-induced pressure converted in ultrasound transducers to voltage signals in a radiofrequency (RF) range (e.g., about 500 Kilohertz, kH, where 1 kH=$10^3$ Hertz and 1 Hertz indicates 1 cycle per second). When tissues absorb heat from pulsed proton beams, they expand and that expansion generates pressure, which propagates through the surrounding tissues as acoustic waves, which can be detected by ultrasound transducers and used to reconstruct the proton-radiation-induced pressures. This technique has drawn wide attention due to its low cost of devices, easy deployment, and capability of real-time dose verification. Ahmad et al. [21] used an analytical model to calculate the proton dose distribution and local pressure rise for beams of different energy (100 and 160 million electron volts, MeV) and spot widths (1, 5, and 10 millimeters, mm, 1 mm=$10^{-3}$ meters) in a water phantom. Jones et al. [22] first observed acoustic emissions from proton beams using a clinical cyclotron, demonstrating possibilities of in vivo proton range verification in clinical settings. Assmann et al. [23] performed a simulation study to detect the Bragg Peak position by measuring the RF signals from ultrasound transducers of single proton pulses, and achieved sub-millimeter accuracy in localizing the Bragg Peak in a water phantom. However, this study only explored ID range verification using a single ultrasound transducer without 3D dose volumetric information. Besides, using a water phantom, that study did not account for the heterogeneity of human tissues. Freijo et al. [24] developed a dictionary-based method to achieve proton range verification based on proton-acoustic signals. However, they performed a simulation study in the 2D computed tomography (CT) images, lacking 3D dose verification. Peng's group conducted several simulation studies [25-27] to verify proton range in 2D or 3D CT images using sparse-view ultrasound detectors distributed over a full 360-degree ring, demonstrating sub-millimeter Bragg peak errors. However, sparse-view detectors in a ring geometry are impractical to deploy during the dose delivery in proton therapy due to mechanical clearance issue and interference with treatment delivery. Recently, a matrix array has been developed for ultrasound imaging 28. It enables real-time 3D imaging while being easy to deploy in clinical settings without mechanical issues or interference with the treatment. A study from the inventors' group [29] showed the feasibility of using a simpler two-dimensional transperineal matrix ultrasound array for prostate dose verification. However, the reconstructed pressure maps are distorted due to the limited-angle view of the matrix array, adversely affecting the dose verification accuracy.

SUMMARY

The inventors realized that reconstructing three-dimensional dose or pressure images from limited-angle ultrasound acquisitions is essentially an ill-conditioned inverse problem, in which deep learning (using neural networks) has demonstrated great merits [30-35]. For example, in X-ray contexts, Huang et al. [36] developed a deep learning model to reconstruct computerized tomography (CT) images from limited-angle X-ray acquisitions, achieving significantly improved root mean squared errors (RMSE). In other X-ray technology, a previous study [37] demonstrated the effectiveness of deep learning in restoring volumetric information from limited-angle cone-beam CT (CBCT). In a purely acoustic context, Cheng et al. [38] showed the feasibility of deep learning to reconstruct the 2D speed of sound images for limited-angle ultrasound tomography using phantom data. The results are promising, although the image quality is still degraded.

Techniques are provided for utilizing deep learning to detect in real time the three-dimensional dose delivered to a subject during proton beam therapy. Here real time indicates within ten seconds of actual occurrence, e.g., a trained model output within ten seconds of the dose being delivered. For example, in some embodiments, it is advantageous to have a delay of 1 second or less. In the example embodiment described below, the delay from actual dose to model output with current computational power is only ~0.2 seconds which is even more advantageous especially for affecting the next pulse delivered by an proton beam source. In some embodiments, real-time also indicates detecting dose changes on the order of 0.1 second with a delay of 10 seconds or less. Reconstruction of a 3De dose image and data I/O, including control of one or more proton beam sources, can take some extra time depending on algorithm and hardware.

In a first set of embodiments, a method executed on a processor for real-time detection of dose delivered to tissue by a proton beam includes retrieving conversion data that indicates values for parameters that convert proton exposure to proton energy dose to acoustic pressure based on values at voxels in medical imagery. Herein, real-time indicates within ten seconds of actual occurrence. The method also includes retrieving a three-dimensional (3D) medical image of a first region of interest inside a first subject. The method still further includes receiving a real-time signal that indicates ultrasound pressure received at a two-dimensional (2D) ultrasound transducer array disposed outside the first subject in contact with the first subject close to the first region of interest. Even further still, the method includes determining a real-time 3D dose delivered in the first region of interest inside the first subject by inputting the real-time signal into a dose detection module that includes at least one neural network. The at least one neural network is trained on multiple instances of a training set. Each instance includes simulated proton dose delivered to a similar region of interest inside a second subject. Each instance also includes simulated pressure generation from that simulated dose based on the conversion data and a similar 3D medical image. Each instance also includes simulated acoustic transmission from the similar region of interest to a similar two-dimensional ultrasound transducer array similarly disposed.

In some embodiments of the first set, the neural network has a multi-scale U-net architecture modified to include a 3D convolution hidden layer. In some of these embodiments, the neural network includes a batch normalization hidden layer after the 3D convolution hidden layer.

In some embodiments of the first set, the neural network has a multi-scale U-net architecture modified to include a dropout hidden layer in a bottom of the U-net between contracting layers and expanding layers.

In some embodiments of the first set, the 3D medical image of the subject and the similar 3D medical image in each instance is segmented into at least four kinds of materials, including air, fat, soft tissue, and bone, each with a different value for a parameter to convert proton dose to pressure. In some of these embodiments a value for the parameter to convert proton dose to pressure in air is replaced with a corresponding value in water.

In some embodiments of the first set, the 3D medical image of the subject and the similar 3D medical image in each instance is a computerized tomography 3D image segmented into at least four kinds of materials, including air, fat, soft tissue, and bone based on Hounsfield unit (HU) value thresholding, each with a different value for a parameter to convert proton dose to pressure.

In some embodiments, the dose detection module includes a first neural network trained on the simulated pressure generation from the simulated dose as output and simulated acoustic transmission from the similar region of interest to a similar two-dimensional ultrasound transducer array as input. In some of these embodiments, the dose detection module includes a second neural network trained on the simulated proton dose as output and the simulated pressure generation from that simulated dose as input.

In some embodiments of the first set, the dose detection module includes a first neural network trained on the simulated proton dose as output and the simulated pressure generation from that simulated dose as input.

In some embodiments of the first set, the dose detection module includes a time-reversal (TR) algorithm that outputs 3D pressure based on acoustic transmission from the region of interest to the two-dimensional ultrasound transducer array using the real-time signal and the conversion data and the 3D medical image as input. In some of these embodiments the TR algorithm is an iterative TR algorithm. In some of these embodiments, the dose detection module includes a first neural network trained on the simulated pressure generation from the simulated dose as output and 3D pressure from the TR algorithm as input.

In some embodiments of the first set, the similar 3D medical image in every instance of the training set is identical to the 3D medical image of the first region of interest inside the first subject.

In some embodiments of the first set, the simulated acoustic transmission from the similar region of interest to a similar two-dimensional ultrasound transducer array includes a different random measurement error in each different instance of the training set.

In some embodiments of the first set, the simulated acoustic transmission from the similar region of interest to a similar two-dimensional ultrasound transducer array includes a different random measurement error in each different instance of the training set.

In some embodiments of the first set, the simulated proton dose includes a different random spatial displacement in each different instance of the training set.

In some embodiments of the first set, the two-dimensional ultrasound transducer array similarly disposed includes a different random spatial displacement in each different instance of the training set.

In other sets of embodiments, a non-transient computer-readable medium or an apparatus or a neural network or a system is configured to perform the steps of one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1B is a block diagram that illustrates an example method for training a model, such as a neural network (NN), using the training set of FIG. 1A, according to an embodiment;

FIG. 3C is a block diagram that illustrates an example of a method for producing an instance for a training set for a deep-learning component of the system of FIG. 3A, according to an embodiment;

FIG. 4 is a flow diagram that illustrates an example of a method for training the deep-learning components of the system of FIG. 3A, according to an embodiment;

FIG. 6 is a flow diagram that illustrates an example of a method for using the trained the deep-learning components of the system of FIG. 3A to provide real-time detection of 3D dose delivered by proton beam therapy, according to an embodiment;

FIG. 7 is a table that illustrates an example list of values for parameters that convert proton dose to acoustic pressure based on intensity values at voxels of a 3D CT scan, according to an embodiment;

FIG. 8b is a table showing example of good performance (small root mean square error, RMSE) between ground truth and outputs from the trained deep-learning components of the system of FIG. 3A, according to an example embodiment;

6

Figure 9:
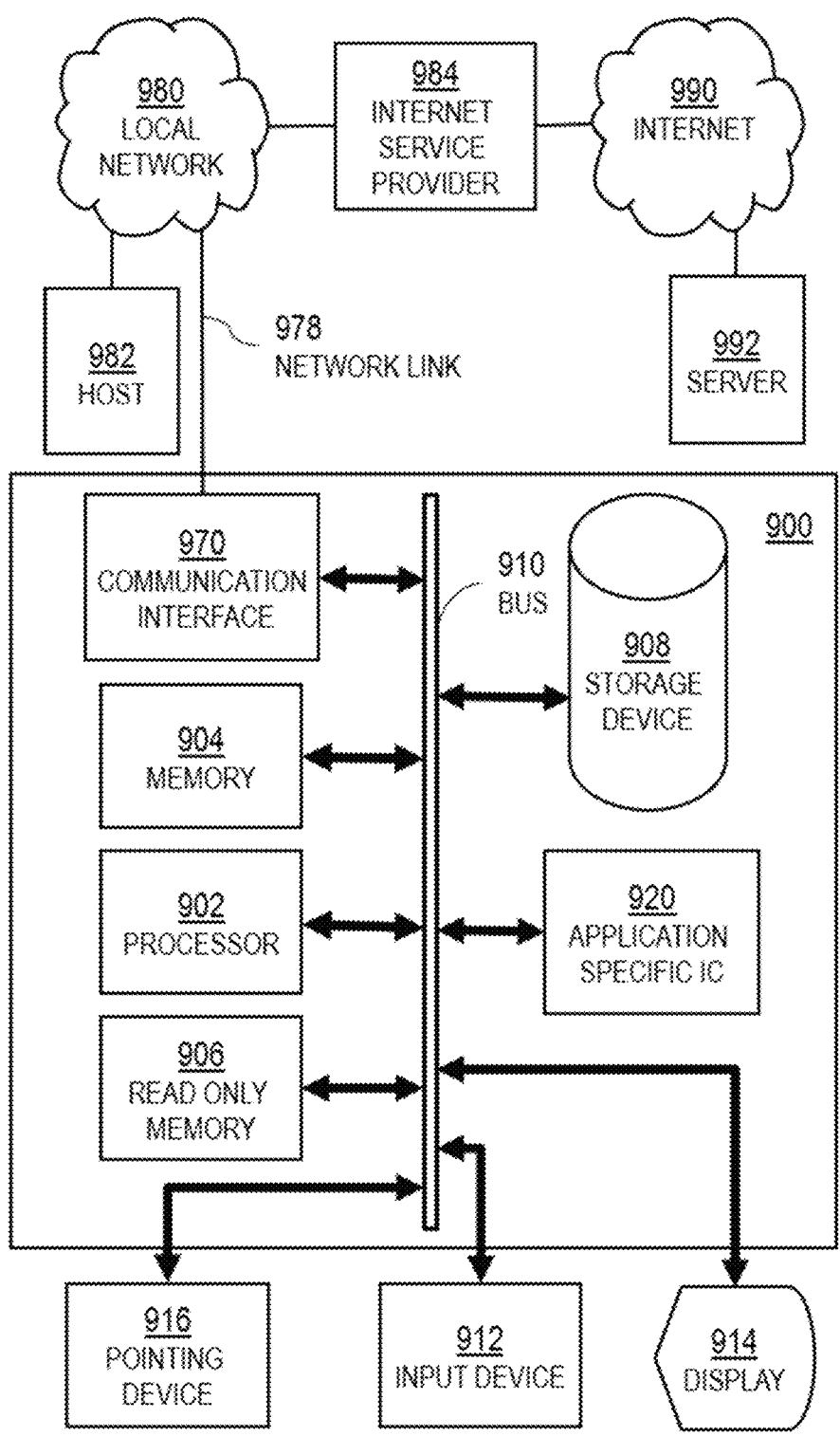
Figure 10:
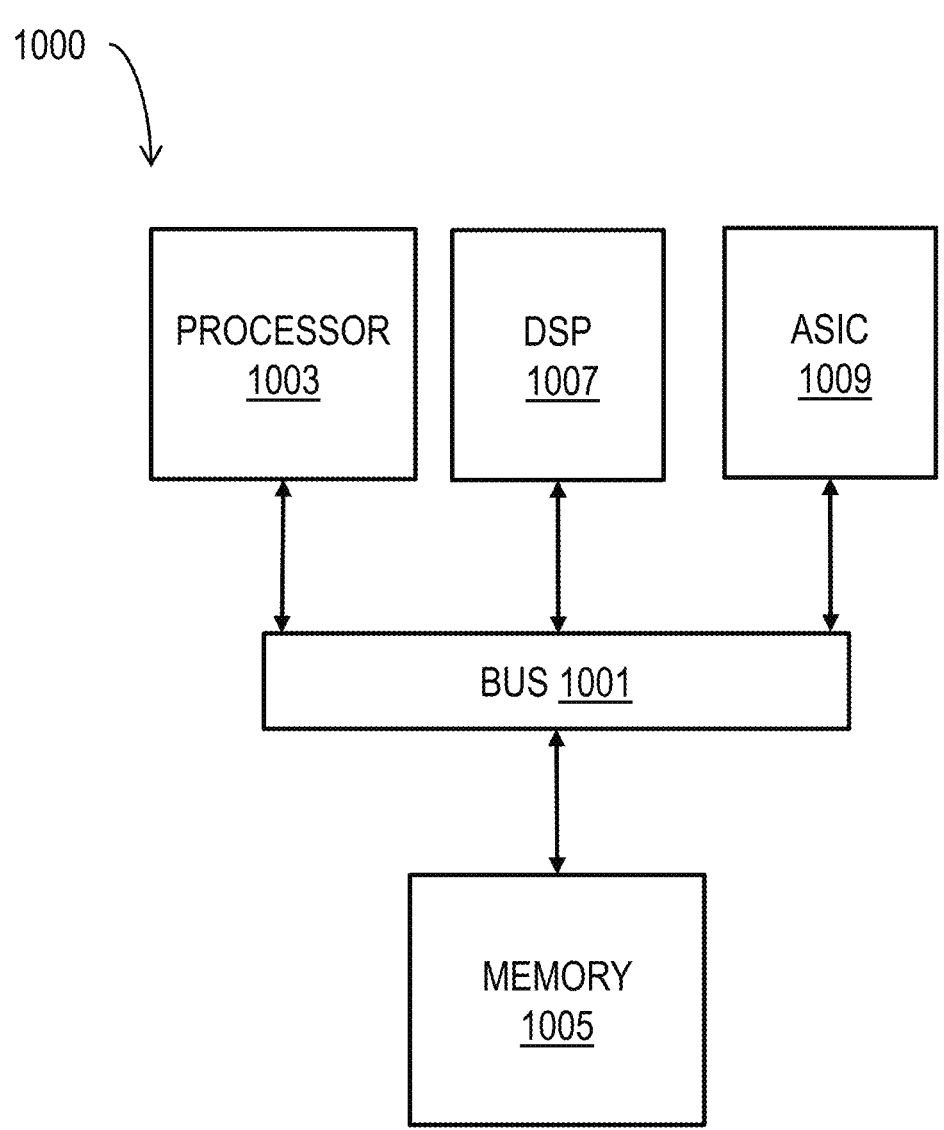

FIG. 9 is a block diagram that illustrates a computer system upon which an embodiment of the invention may be implemented; and FIG. 10 illustrates a chip set upon which an embodiment of the invention may be implemented.

DETAILED DESCRIPTION

A method, apparatus and system are described for are provided for utilizing deep learning to detect the three-dimensional dose delivered during proton beam therapy. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of treating a prostate tumor in a male human subject using a proton beam treatment plan and two-dimensional (2D) ultrasound transducer array to output RF voltages, which 2D array is disposed in space external to but adjacent to a perineum of the subject. However, the invention is not limited to this context. In other embodiments, the subject is a female human or non-human animal or plant or other organism or tissue and the treatment plan is for a tumor or other target located in a different organ or organs, and the 2D ultrasound transducer array is disposed external to but adjacent to other portions of the subject's anatomy.

1. OVERVIEW 1.1. Neural Network Overview

Figure 1A:
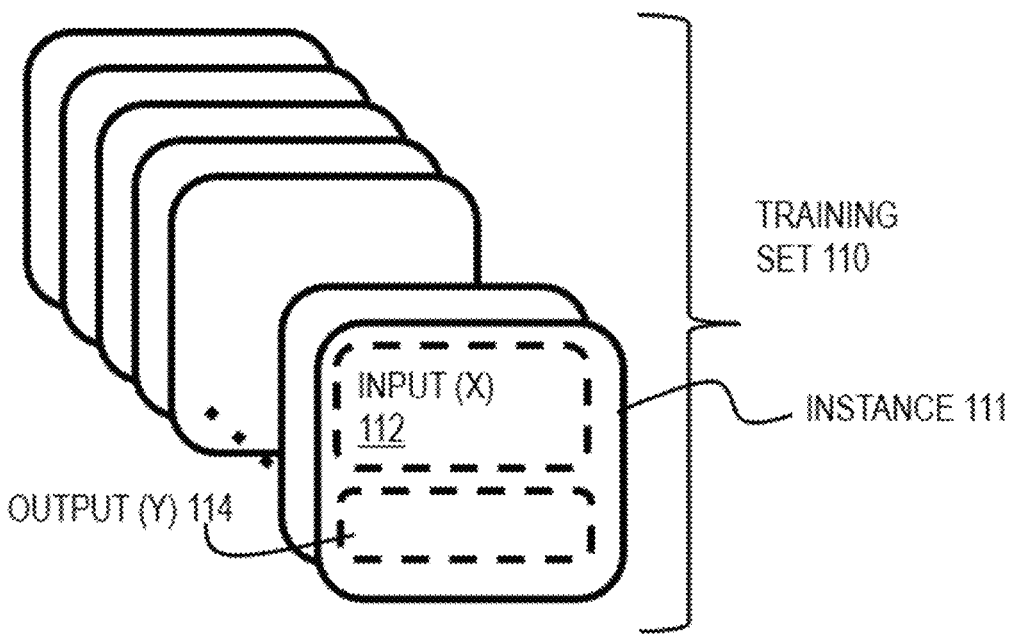
FIG. 1A is a block diagram that illustrates an example training set, according to an embodiment.

FIG. 1A is a block diagram that illustrates an example training set 110, according to an embodiment. The training set 110 includes multiple instances, such as instance 111. The instances 111 for the set 110 are selected to be appropriate.

During machine learning, a model M is selected which is appropriate for the purpose and data at hand. One or more of the model M adjustable parameters P is uncertain for that particular purpose and the values for such one or more parameters are learned automatically. Innovation is often employed in determining which model to use and which of its parameters P to fix and which to learn automatically. The learning process is typically iterative and begins with an initial value for each of the uncertain parameters P and adjusts those prior values based on some measure of goodness of fit of its Model output $Y_M$ with known results Y for a given set of values for input context variables X from an instance 201 of the training set 200.

Figure 2A:
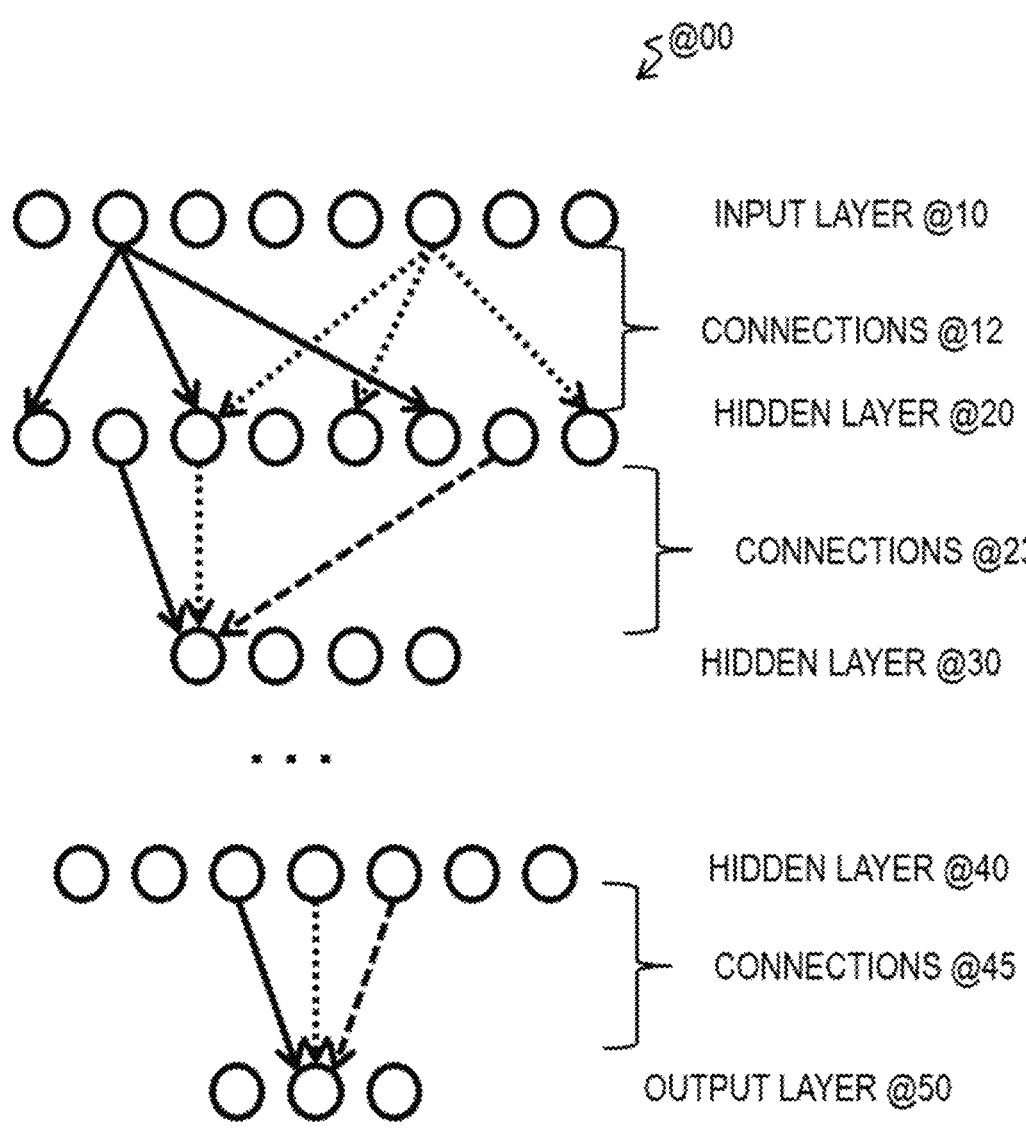
FIG. 2A is a block diagram that illustrates an example neural network that can be trained, according to various embodiments.
Figure 2B:
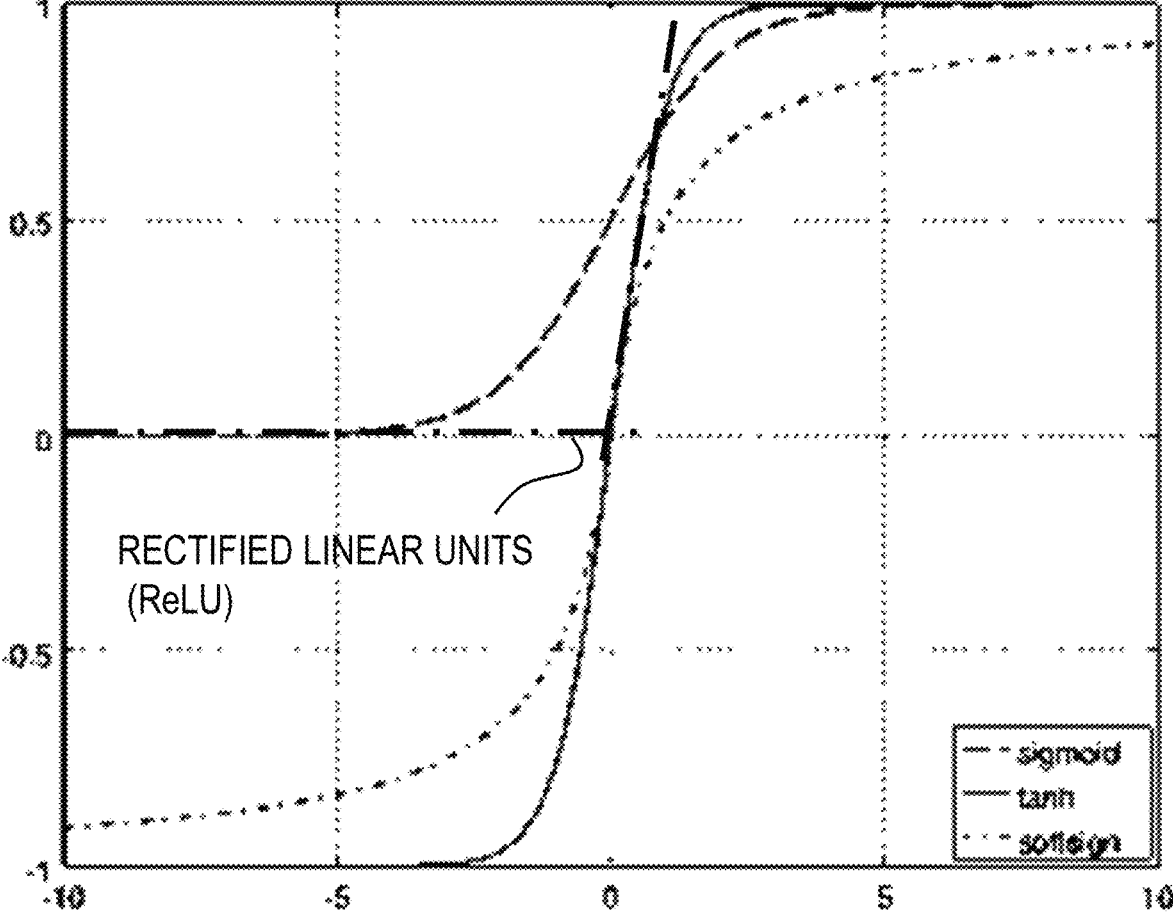
FIG. 2B is a plot that illustrates example activation functions used to combine inputs at any node of a feed forward neural network, according to various embodiments.

FIG. 2B is a block diagram that illustrates an example automatic process for learning values for uncertain parameters P 212 of a chosen model M 210. The model M 210 can be a Boolean model for a result Y of one or more binary values, each represented by a 0 or 1 (e.g., representing FALSE or TRUE respectively), a classification model for membership in two or more classes (either known classes or self-discovered classes using cluster analysis), other statistical models such as multivariate regression or neural networks, or a physical model, or some combination of two or more such models. A physical model differs from the other purely data-driven models because a physical model depends on mathematical expressions for known or hypothesized relationships among physical phenomena. When used with machine learning, the physical model includes one or more parameterized constants, such as propagation loss coefficients, that are not known or not known precisely enough for the given purpose.

During training depicted in FIG. 2B, the model 210 is operated with current values 212 of the parameters P, including one or more uncertain parameters of P (initially set arbitrarily or based on order of magnitude estimates) and values of the context variables X from an instance 201 of the training set 200. The values 216 of the output $Y_M$ from the model M, also called simulated measurements, are then compared to the values 224 of the known result variables Y from the corresponding instance 201 of the training set 200 in the parameters values adjustment module 230.

The parameters values adjustment module 230 implements one or more known or novel procedures, or some combination, for adjusting the values 212 of the one or more uncertain parameters of P based on the difference between the values of $Y_M$ and the values of Y. The difference between $Y_M$ and Y can be evaluated using any known or novel method for characterizing a difference, including least squared error, maximum entropy, fit to a particular probability density function (pdf) for the errors, e.g., using a priori or a posterior probability. The model M is then run again with the updated values 212 of the uncertain parameters of P and the values of the context variables X from a different instance of the training set 200. The updated values 216 of the output $Y_M$ from the model M are then compared to the values of the known result variables Y from the corresponding instance of the training set 200 in the next iteration of the parameter values adjustment module 230.

The process of FIG. 2B continues to iterate until some stop condition is satisfied. Many different stop conditions can be used. The model can be trained by cycling through all or a substantial portion of the training set. In some embodiments, a minority portion of the training set 200 is held back as a validation set. The validation set is not used during training, but rather is used after training to test how well the trained model works on instances that were not included in the training. The performance on the validation set instances, if truly randomly withheld from the instances used in training, is expected to provide an estimate of the performance of the learned model in producing $Y_M$ when operating on target data X with results Y that are not already known. Typical stop conditions include one or more of a certain number of iterations, a certain number of cycles through the training portion of the training set, producing differences between $Y_M$ and Y less than some target threshold, producing successive iterations with no substantial reduction in differences between $Y_M$, and errors in the validation set less than some target threshold, among others.

Deep learning refers to using one or more neural networks within the model 110. Deep learning is widely used in image processing and natural language processing. FIG. 2A is a block diagram that illustrates an example neural network 200, according to various embodiments. A neural network 200 is a computational system, implemented on a general-purpose computer, or field programmable gate array, or some application specific integrated circuit (ASIC), or some neural network development platform, or specific neural network hardware, or some combination. The neural network is made up of an input layer 210 of nodes, at least one hidden layer 220, 230 or 240 of nodes, and an output layer 250 of one or more nodes. Each node is an element, such as a register or memory location, that holds data that indicates a value. The value can be code, binary, integer, floating point or any other means of representing data, including arrays of values in vectors or matrices. Values in nodes in each successive layer after the input layer in the direction toward the output layer is, based on the values of one or more nodes in one or more previous layers. The nodes in one layer that contribute to the next layer are said to be connected to the node in the later layer. Connections 212, 223, 245 are depicted in FIG. 2A as arrows. The values of the connected nodes are combined at the node in the later layer and weighted using some activation function with scale and bias (also called weights) that can be different for each connection. Neural networks are so named because they are modeled after the way neuron cells are connected in biological systems. A fully connected neural network has every node at each layer connected to every node at any previous or later layer.

FIG. 2B is a plot that illustrates example activation functions used to combine inputs at any node of a neural network. These activation functions are normalized to have a magnitude of 1 and a bias of zero; but when associated with any connection can have a variable magnitude given by a weight and centered on a different value given by a bias. The values in the output layer 250 depend on the values in the input layer and the activation functions used at each node and the weights and biases associated with each connection that terminates on that node. The sigmoid activation function (dashed trace) has the properties that values much less than the center value do not contribute to the combination (a so called switch off effect) and large values do not contribute more than the maximum value to the combination (a so called saturation effect), both properties frequently observed in natural neurons. The tanh activation function (solid trace) has similar properties but allows both positive and negative contributions. The softsign activation function (short dash-dot trace) is similar to the tanh function but has much more gradual switch and saturation responses. The rectified linear units (ReLU) activation function (long dash-dot trace) simply ignores negative contributions from nodes on the previous layer, but increases linearly with positive contributions from the nodes on the previous layer; thus, ReLU activation exhibits switching but does not exhibit saturation. In some embodiments, the activation function operates on individual connections before a subsequent operation, such as summation or multiplication; in other embodiments, the activation function operates on the sum or product of the values in the connected nodes. In other embodiments, other activation functions are used, such as kernel convolution.

An advantage of neural networks is that they can be trained to produce a desired output from a given input without knowledge of how the desired output is computed. There are various algorithms known in the art to train the neural network on example inputs with known outputs. Typically, the activation function for each node or layer of nodes is predetermined, and the training determines the weights and biases for each connection. A trained network that provides useful results, e.g., with demonstrated good performance for known results, is then used in operation on new input data not used to train or validate the network.

In some neural networks, the activation functions, weights and biases, are shared for an entire layer. This provides the networks with shift and rotation invariant responses. The hidden layers can also consist of convolutional layers, pooling layers, fully connected layers and normalization layers. The convolutional layer has parameters made up of a set of learnable filters (or kernels), which have a small receptive field. In a pooling layer, the activation functions perform a form of non-linear down-sampling, e.g., producing one node with a single value to represent two or more nodes in a previous layer. There are several non-linear functions to implement pooling among which max pooling is the most common. A normalization layer simply rescales the values in a layer to lie between a predetermined minimum value and maximum value, e.g., 0 and 1, respectively. A dropout layer improves generalization and prevents overfitting by randomly disabling a proportion of neurons during training, encouraging the network to learn more robust features.

A common network architecture found useful in medical 2D and 3D imaging is the U-NET. The network consists of a contracting path and an expansive path, which gives it the u-shaped architecture. The contracting path is a typical convolutional network that consists of repeated application of convolutions, each followed by a rectified linear unit (ReLU) and a max pooling operation. During the contraction, the spatial information is reduced while feature information is increased, e.g., more important features covering more voxels emerge. The expansive pathway combines the important features with their original spatial resolution through a sequence of up-convolutions and concatenations with high-resolution information from the contracting path.

1.2. Structures for Real-Time Proton Beam Dose Detection

Figure 3A:
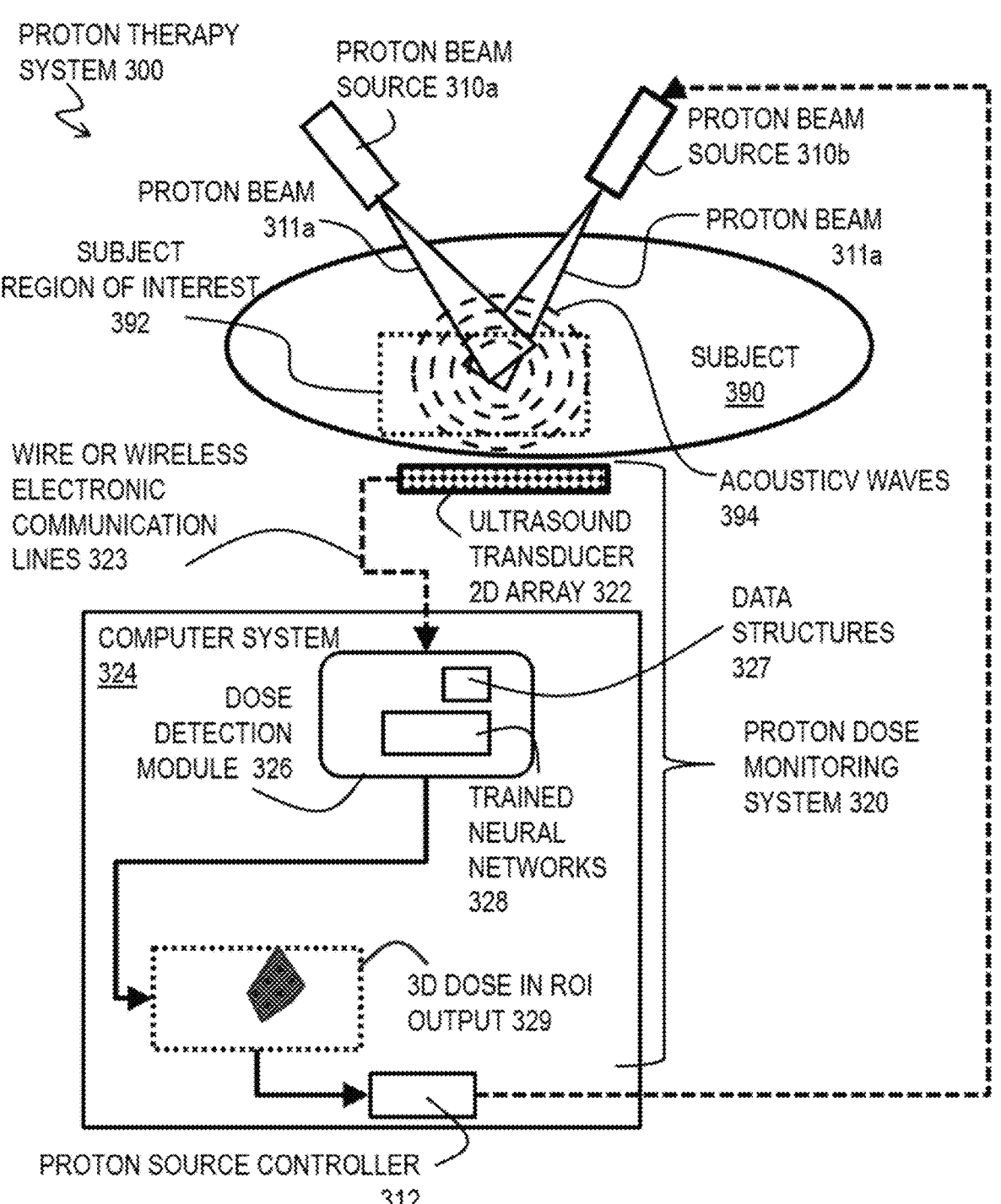
FIG. 3A is a block diagram that illustrates an example of a system configured to detect 3D dose delivered by one or more proton beams in real-time, according to an embodiment.

FIG. 3A is a block diagram that illustrates an example of a system 300 configured to detect 3D dose delivered by one or more proton beams in real-time, according to an embodiment. Although a subject 390 and a region of interest (ROI) 392 inside subject 390 and acoustic waves 394 propagating inside subject 390 are depicted for purposes of illustration, neither subject 390 nor subject's region of interest 392 nor acoustic waves 394 is part of system 300.

System 300 includes one or more proton beam sources 310a, 310b (collectively referenced hereinafter as proton beam source 310) that each is configured to produce a proton beam, e.g., proton beams 311a, 311b (collectively referenced hereinafter as proton beam 311). Proton beams 311 are directed into a subject 390, either simultaneously or sequentially, for short or long duration. Tissue inside subject 390 absorbs proton energy with increasing efficiency as the protons slow down until near complete absorption takes place at a Bragg Peak, beyond which proton flow and energy absorption falls off dramatically. The Bragg peak is represented by the wide distal end of the depicted proton beams 311. A proton beam therapy plan is designed to place the Bragg peak at a target, such as a tumor, in a region of interest (ROI) 392 inside the subject while sparing as much as possible tissues surrounding the target. For this reason, some proton beam therapy plans include directing proton beams onto a target from multiple different directions, e.g., using multiple proton beam sources 310 or moving a single proton beam source 310 to vary the direction of the proton beam at different times, while still placing the Bragg Peak on the same target. When tissue absorbs proton beam energy, the tissue expands sufficiently to generate a pressure wave at ultrasound (US) frequencies (above 40 kilohertz). For example, one or more US waves 394 at or near 500 kHz are generated.

The system 300 includes a two-dimensional (2D) ultrasound transducer array 322 configured to be disposed outside the subject 390 but in contact with the subject 390 close enough to the ROI 392 to detect acoustic waves 394 without interfering with the delivery of proton beams 311 from proton beam source 310. A clinical translatable matrix ultrasound array can be used to collect proton-acoustic (PA) signals. The pressure time series arrives at each transducer in the 2D array 322 is converted to a electronic signal, such as current or voltage time series, that can be captured and processed using readily available radio frequency (RF) equipment. Any clinically used ultrasound array with the appropriate frequency band (matching well with the proto-acoustic signal frequency) would be suitable for proto-acoustic imaging. The configuration of the array, whether linear, curved, or matrix, depends solely on the imaging targets. The numbers of the transducer on the linear array is typically 128 element, and the numbers of the transducer on the linear array is typically 128 element, 256 element, and 512 element. The numbers of the transducer on the matrix array is typically 256 element and 1024 element.

The system 300 includes computer system 324 and wired or wireless electronic communication lines 323 that transmit the electronic RF signal into computer system 324. The computer system 324 of system 300 includes one or more local or remote processors in direct or networked communication, such as depicted in FIG. 9 and FIG. 10 and described in more detail below. The computer system 324 of system 300 includes dose detection module 326 that receives the RF signal from array 322 and outputs a 3D dose data structure 329 for the ROI 392 in real-time.

Dose detection module 326 includes software or hardware processing or some combination that implements one or more trained neural networks 328. In some embodiments, a deep cascaded convolutional neural network (DC-CNN) reconstructs 3D high-quality radiation-induced pressures using detected PA signals from a matrix array. Furthermore, the DC-CNN can derive 3D dosimetry from pressures for dose verification in proton therapy. Thus, the system and method according to several embodiments are configured to increase precision and reduce inaccuracies of typical dose verification methods. The dose detection module 328 also includes one or more data structures 327 that hold data that indicates at least a 3D medical image of the ROI 392 of subject 390 and values at each voxel of the medical image for parameters that convert proton dose delivered to tissue pressure increase.

In some embodiments, the 3D dose data structure 329 is used by a proton source controller 312, e.g., to determine whether and when to stop delivering a proton beam or when and where to deliver another proton beam onto the target in the ROI 392, or some combination.

Figure 3B:
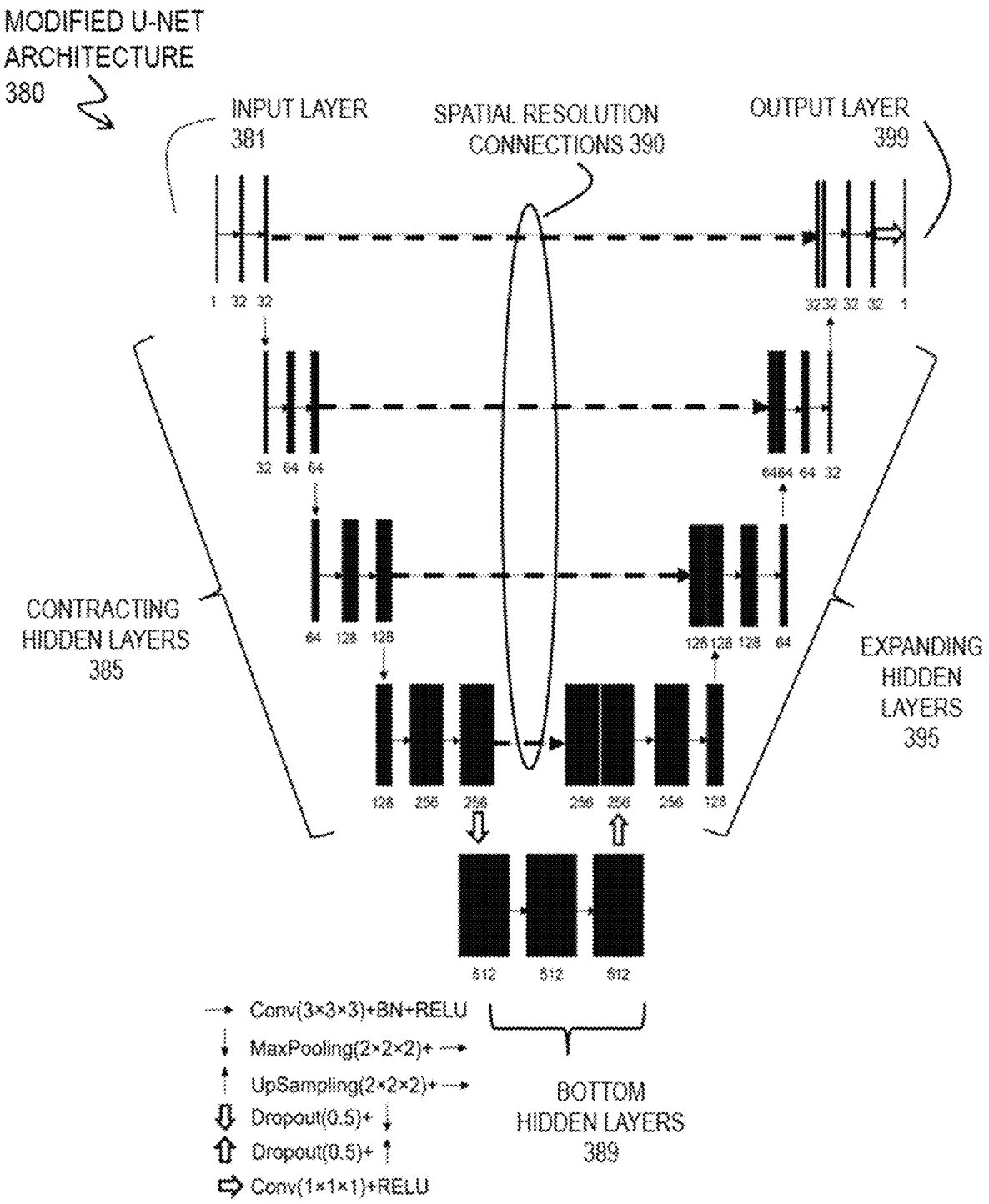
FIG. 3B is a block diagram that illustrates examples of a modified U-Net architecture for a deep-learning component of the dose detection module, according to an embodiment.

FIG. 3B is a block diagram that illustrates examples of a modified U-Net architecture 380 for a deep-learning component of the system of FIG. 3A, according to an embodiment. The input layer 381 is an array of values representing the voxel values in a 2D or 3D image, such as several time points in the 2D RF signal out of the transducer array or several axial locations of CT slices in a 3D medical image. The input layer may have been provided, in some embodiments, by an input processing module that combines over-sampled data into a smaller sample size suitable for the computing power and performance desired, or even the conversion of the 2D time series from the transducer array into a 3D spatial image of pressure produced by a time-reversal (TR) algorithm, such as the iterative TR algorithm. This is considered one channel of information as indicated by the value 1 depicted below the input layer 381. The total size of the input layer (e.g., 100×100×10=100,000 nodes) is represented by the height of the line of the first channel and represents high resolution data. In the illustrated embodiment each dimension is halved at each of 4 sets of contractions, so it is advantageous for the number of pixels in each dimension be a factor of 24 (i.e., 16). Thus, in some embodiments, the original input layer represents a volume of about 128×128×16 voxels (264144 voxels) or some factor thereof.

The input layer is then connected by a 3D convolution kernel of size 3×3×3 a batch normalization (BN) layer and a RELU activation function. Batch normalization is a method used to make training of artificial neural networks faster and more stable through normalization of the layers' inputs by re-centering and re-scaling. The activation function is used to introduce non-linearity to the model representation, including switching but not saturation effects. The input layer is connected to each of a set of hidden layers, each hidden layer of the same size/resolution to produce multiple channels of information, based on different weights to be determined during training. In the illustrated embodiment 32 channels are produced; but in other embodiments more or fewer channels are produced. A second convolution block follow 3 to generate 32 new channels of information from the output of the previous convolution block. But, in other embodiments different kernel numbers (e.g. 16) and size (e.g. 5*5*5) and different activation functions can be used. These 32 channels of full size/resolution are then each connected to a second set of hidden layers by a 3D convolution kernel of size 3×3×3 using RELU and BN to amplify the significant features in these channels during training. The use of 3D convolution in these channels is a modification of the conventional U-Net architecture that used only 2D convolution (e.g., 3×3 convolution kernels).

The 32 channels of full size/resolution channels output by the second set of convolutions are then contracted to a lesser size resolution (i.e., smaller size/coarser resolution) by max pooling layer with 3D convolution. In the illustrated embodiment, the max pooling is a 3D pool of 2×2×2 (i.e., a cube of 2 voxels by 2 voxels by 2 voxels is replaced by a single voxel holding the maximum value among those 8 values); but, in other embodiments a different degree of pooling (e.g., 3×3×3) or other method of producing the pooled value (e.g., averaging or minimum value or convolution with a stride of >2) may be used. In the illustrated embodiment the contracted layer is also subjected to 3D convolution. Thus, in the illustrated embodiment, the 3×3×3 3D convolution is using the maximum values in each of 9 different cubes of 8 voxels. The number of channels is then doubled by connecting each contracted layer to two other layers again using 3D convolution with RELU and BN on a 3×3×3 set of nodes. Again, in other embodiments a different degree of 3D convolution or number of channels can be used. These 64 channels of lesser size/resolution are then each connected to a second set of hidden layers by a 3D convolution kernel of size 3×3×3 using RELU and BN to amplify the significant features in these 64 channels during training. Another two convolution blocks with doubled kernel number (64) are used to generate advanced features from the contracted features.

Contracting to lesser resolution and increasing the number of channels continues in a similar way in one or more subsequent sets of hidden layers. The hidden layers that engage in lessening size/resolution while increasing the number of channels are called contracting hidden layers 385. In the illustrated embodiment, contracting hidden layers 385 continues until there are 512 channels at 1/16 the original spatial resolution. In other embodiments a different number of contractions and channel increases are used.

In the illustrated embodiment, the last contraction includes a dropout layer of 0.5 meaning half of the neurons in the layer are randomly dropped out during training. That is, a different half of the nodes are used with one training instance than are used in a different training instance. In other embodiments, a different dropout rate is used The use of a dropout layer is another modification from the conventional U-Net architecture.

The hidden layers with the least size/resolution and most channels are called the bottom hidden layers 389 of the U-Net architecture, or simply the bottom. In the illustrated embodiment, the bottom hidden layers 389 include two successive 3D convolution blocks for each channel. In other embodiments, different convolution block numbers and settings (including convolutional kernel number and size, and activation function) can be used.

After the bottom hidden layers 389, the expanding hidden layers occur. In the illustrated embodiment the first expansion from the bottom hidden layers 389 includes a dropout layer in another modification of the conventional U-Net architecture. At each expansion, the first set of hidden layers increases the resolution of each channel but decreases the number of channels through a sequence of up-convolutions and concatenations with high-resolution features from the contracting path. Up convolution combines convolution with up sampling. In the illustrated embodiment, the convolution is a 3D convolution and the up-sampling is a 3D up-sampling in a further modification from the conventional U-Net architecture. The concatenation appends the last set of contracting hidden layers with the same size/resolution and number of channels to the up-convolution output as indicated by the spatial resolution connections 390. Thus, in the first set of channels in the expanding hidden layers 395, the number of channels input to the next 3D convolution is repeated, e.g., (256 256) or (128 128) or (64 64) or (32 32). The concatenated and up-sampled layers are then subjected to 3D convolution to reduce the number of channels in a manner that matches the down-sampling in the corresponding contracting hidden layer. The 3D convolution decreasing the number of channels is repeated at each size/resolution before being up-sampled again at the next expansion stage.

While the illustrated embodiment shows an 3D up-sampling of 2×2×2 and a dropout of 0.5 entering the expanding hidden layers 395, in other embodiments, other 3D up-sampling sizes and dropout rates are used.

The lessening size/resolution from the input layer 381 through the contracting layers 385 can be associated with the left-side downward stroke during writing the letter U, the bottom layers 389 can be associated with the horizontal stroke when writing the letter U, and the increasing size/resolution from the bottom layers 389 through the expanding layers 395 to the output layer 399 can be associated with the right-side upward stroke during writing the letter U. Hence the name of the architecture is the U-Net.

FIG. 3B illustrates various modifications to the conventional U-Net architecture. In some embodiments, the neural network has a multi-scale U-net architecture modified to include a 3D convolution hidden layer. In some of these embodiments, the neural network includes a batch normalization (BN) hidden layer after the 3D convolution hidden layer. In some embodiments, the neural network has a multi-scale U-net architecture modified to include a dropout hidden layer in a bottom of the U-net between contracting layers and expanding layers.

1.2. Method for Training Deep Learning Component of Real-Time Proton Beam Dose Detection The successful performance of system 300 depends on adequate training for the one or more neural networks 328 in the dose detection module 326, which in turn depends on having a large number of training instances that cover the variations among subjects and tissues and disposition of the 2D ultrasound transducer array and errors in the determination of each. It was determined that there were few instances of directly measured invasive dose determinations made in concert with 2D US transducer arrays. To compensate, simulations were used to generate the ground truth that the neural networks are expected to recover. To prevent over- fitting to the exact simulations, the training set was aug- mented by instances with slight random changes in therapy plans, distribution of tissues in the region of interest, mea- surement errors, disposition of and makeup of 2D ultrasound transducer arrays, among other aspects, alone or in some combination. Thus, each instance includes simulated proton dose delivered to a similar region of interest inside a second subject and simulated pressure generation from that simu- lated dose based on the conversion data and a similar 3D medical image and simulated acoustic transmission from the similar region of interest to a similar two-dimensional ultrasound transducer array similarly disposed.

In some embodiments, the similar 3D medical image in every instance of the training set is identical to the 3D medical image of the region of interest inside the subject to be treated with proton beam therapy, e.g., the second subject is the same as the patient to be treated. Thus, the similar 3D medical image in every instance of the training set is identical to the 3D medical image of the first region of interest inside the first subject. In other embodiments, a population of similar patients undergoing similar proton beam therapy is used, e.g., a population of males of similar age, weight and height undergoing prostate cancer treat- ment. In some embodiments, the simulated acoustic trans- mission from the similar region of interest to a similar two-dimensional ultrasound transducer array includes a dif- ferent random measurement error in each different instance of the training set. In some embodiments, the simulated proton dose includes a different random spatial displacement in each different instance of the training set. In some embodiments, the two-dimensional ultrasound transducer array similarly disposed includes a different random spatial displacement in each different instance of the training set. In some embodiments, the neural network is trained a few days in advance of the treatment using the same 3D medical image for the same patient with the same transducer array disposed in the same way on the patient, but different measurement errors and uncertainties are randomly added to different instances in the training set. The training set can be augmented also by applying transformations, such as trans- lations, rotations, and deformations, to the original datasets.

FIG. 3C is a block diagram that illustrates examples of a process 303 for producing an instance for a training set for a deep-learning component 328 of the dose detection mod- ule 326, according to an embodiment. Each instance is generated by simulation starting with a 3D medical image 330 for the region of interest, such as a CT scan or a lower resolution cone beam computerized tomography (CBCT) scan or a MRI scan. The region of interest includes all or most of the volume that includes the path of proton beams to the target and the path of acoustic waves from the target to the 2D ultrasound transducer array. To reduce computa- tional power demands and noise, some voxels can be aver- aged or otherwise combined so that the ROI can be expressed in a reasonable number of voxels, e.g, 100 by 100 by 10. A CT scan is especially useful because it indicates X-ray absorption at each voxel and proton beam absorption is expected to be somewhat correlated with X-ray absorp- tion. In any case, 3D CT imagery can discriminate various tissue types, especially drastic density differences between air, water, fat, bone and soft tissue such as organs and muscle. The 3D medical image can be an actual medical scan or the average of several scans from the same person or different persons who are similar in ways described above.

A data structure 331 is produced with a different value for a parameter to convert proton exposure to absorbed proton energy (dose) or to pressure at each voxel, or both, based on segmenting the 3D medical image 330. For example, the 3D medical image of the subject and the similar 3D medical image in each instance is segmented into at least four kinds of materials, including air, fat, soft tissue, and bone, each with different properties related to absorbing proton energy and raising pressure to expand. In some embodiments, a value for a parameter to convert proton exposure to pressure in air is replaced with a value for the parameter to convert proton exposure to pressure in water. Thus, the 3D medical image of the subject and the similar 3D medical image in each instance is segmented into at least four kinds of materials, including air, fat, soft tissue, and bone, each with a different value for a parameter to convert proton exposure to proton energy dose to pressure. In some embodiments the simulated propagation of acoustic waves is disrupted by pockets of air, so a value for a parameter to convert proton dose to pressure in air is replaced with a value for the parameter to convert proton dose to pressure in water. In an example embodiment described in more detail below, com- puterized tomography (CT) 3D image segmented into at least four kinds of materials, including air, fat, soft tissue, and bone based on Hounsfield unit (HU) value thresholding, each with a different value for a parameter to convert proton exposure or dose to pressure. Any method may be used to convert segmented 3D medical imagery to proton absorption and thermal expansion properties. One example method is presented in detail in the examples section using the Table depicted in FIG. 7.

The absorption of proton beam energy is then simulated based on the 3D medical image 330 or parameters 331, and a proton beam therapy plan to produce simulated proton dose delivery. 332 in the region of interest. In some embodi- ments this is a time series extending over several seconds to minutes. In some embodiments the proton exposure is a single burst or pulse of short duration (e.g., a few micro- seconds, μsec, $1 \ \mu sec = 10^{-6}$ seconds [ ). The integrated absorption over the pulse is computed as the delivered dose. This constitutes a desired output, designated "ground truth" Y2, from a neural network of the dose detection module 328 in some embodiments. To augment the number of instances, different random deviations from the proton beam therapy plan, which deviations are commensurate with the precision of proton sources 310 and patient positioning, is introduced in different instances. Any method may be used to convert proton beam exposure to absorption and dose delivered. One example method is presented in detail in the examples section.

Once the proton energy dose delivered is computed for each voxel in the region of interest, the pressure induced in the voxel can be derived using the parameters in data structure 331 and presented in data structure 334. This constitutes a desired output, designated "ground truth" Y1, from a different neural network of the dose detection module 328 in some embodiments and the input X2 for the neural network that outputs proton dose delivered, referenced above. Any method may be used to convert proton beam dose to pressure, e.g., using the thermal expansion property of the material associated with the voxel by the segmenta- tion process. An example method is presented in detail in the examples section.

From the pressure produced by the absorption of proton energy and stored in data structure 334, a sound wave is initiated. The propagation of that sound wave is simulated in module 336 to produce a simulated RF signal output by 2D ultrasound transducer array, e.g., a time series of voltage at each transducer in the array. That time series is stored in a data structure 338 and used as input X1, or to produce input X1, for a neural network.

The process illustrated in FIG. 3C is repeated for each instance generated for the training set for the neural networks 328 of the deep learning by the dose detection module 326.

Figure 3D:
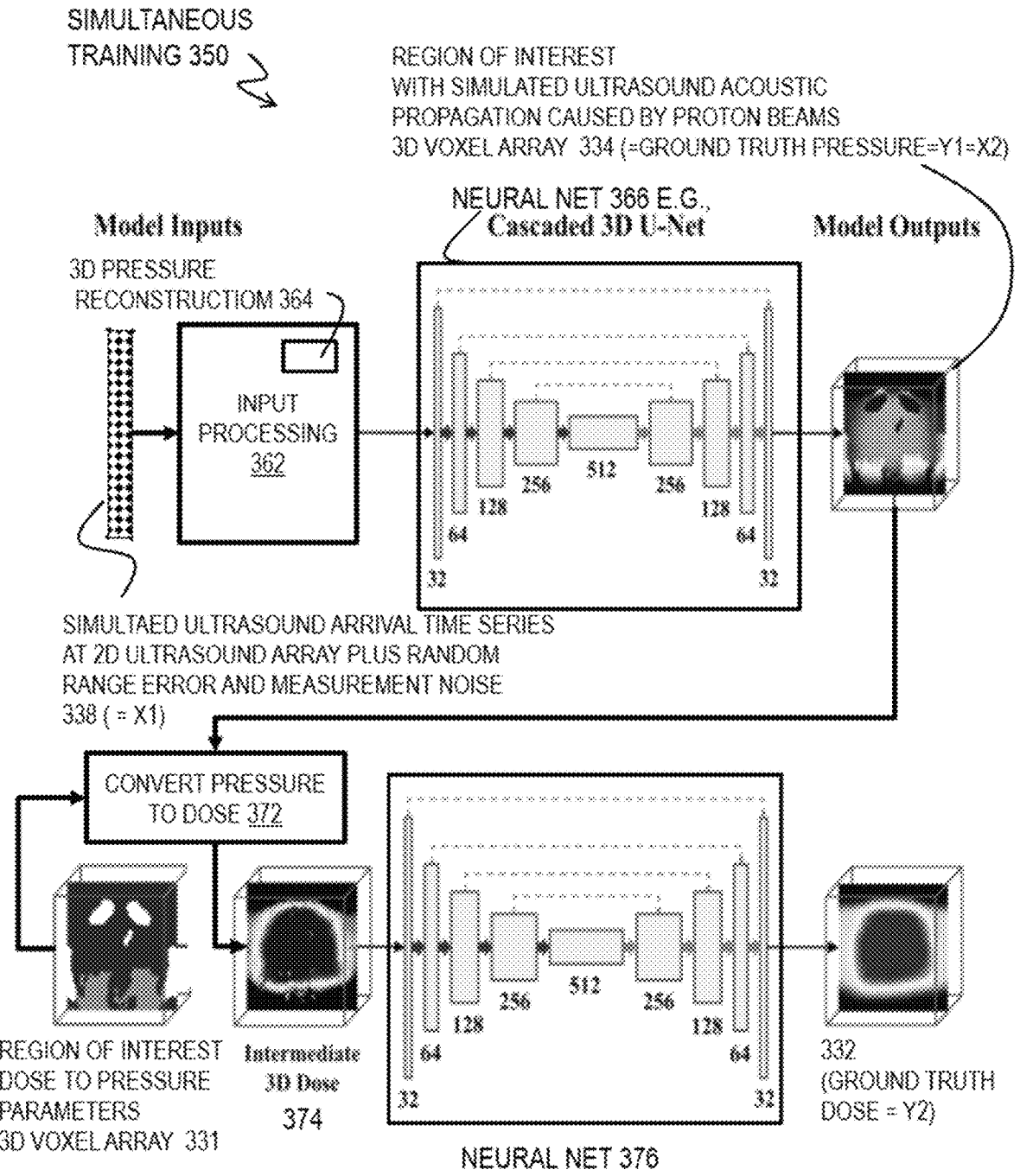
FIG. 3D is a block diagram that illustrates an example of a process for training the deep learning components of the dose detection module, according to an embodiment.

FIG. 3D is a block diagram that illustrates an example of a process 360 of training the deep learning components of the dose detection module 328, according to an embodiment. In this embodiment, the training set is used for simultaneous training of two or more neural networks. One neural network 366 corrects or enhances a 3D pressure map based on the output from the 2D US transducer array; and the other neural network 376 correct a proton energy dose delivery when the pressure output by neural network 366 is used with the conversion parameters of data structure 331. Thus, the dose detection module 326 includes a first neural network 366 trained on the simulated pressure generation from the simulated dose as output and simulated acoustic transmission from the similar region of interest to a similar two-dimensional ultrasound transducer array as input. In this embodiment, the dose detection module 326 includes a second neural network 376 trained on the simulated proton dose as output and the simulated pressure generation from that simulated dose as input. In some embodiments, neural network 366 is omitted and the output from input processing module 362 is used directly by module 372. In this case, the dose detection module 326 includes a first neural network 376 trained on the simulated proton dose as output and the simulated pressure generation from that simulated dose as input.

The simulated time series of RF signals output from the 2D ultrasound transducer array 338 is used as input X1 to an input processing module 362 that outputs values for an input layer of neural net 366. In some embodiments, the input processing is a simple normalization. In some embodiments, the input processing includes a 3D pressure reconstruction module 364 that comprises either a third neural network that moves from 2D US time series signals to 3D pressure or a time reversal (TR) algorithm, such as the iterative TR algorithm. The TR algorithm propagates received ultrasound waves backward in time to a pressure source that serves as an initial guess for the 3D pressure field. Thus, in some embodiments, the dose detection module includes a time-reversal (TR) algorithm that outputs 3D pressure based on acoustic transmission from the region of interest to the two-dimensional ultrasound transducer array using the real-time signal and the conversion data based on the 3D medical image as input.

The initial guess for a 3D pressure map output by input processing module 362 is expected to deviate from the ground truth pressure 334, and the neural network 336 is trained (weights and biases modified) to minimize these deviations. In the illustrated embodiment, a modified U-Net architecture, found useful for medical imagery interpretation, is used for neural network 366, as described in more detail above with reference to FIG. 3B.

The refined pressure field output by the neural network 336 is combined with the 3D data structure of dose to pressure parameters in module 372 to produce an initial guess for the 3D dose. This initial guess output by module 372 is expected to deviate from the ground truth dose 332, and the second neural network 376 is trained (weights and biases modified) to minimize these deviations. In the illustrated embodiment, a modified U-Net architecture, found useful for medical imagery interpretation, is also used for neural network 376. The initial weights and biases in the two neural networks 366 and 376 are modified based on the differences between the output and ground truth values for the 3D pressure and 3D dose, until the deviations for both are minimized for the bulk of the training set, some instances held back for validation of the trained networks 336 and 376.

FIG. 4 is a flow diagram that illustrates an example of a method 400 for training the deep-learning components of the system of FIG. 3A, according to an embodiment. Although steps are depicted in FIG. 4, and in subsequent flow diagram FIG. 6, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 401, 3D medical scans from one or more subjects are collected for a region of interest and proton-exposure-to-pressure parameter values by voxel are determined. This step includes any manual or automated segmentation of the region of interest into sub-regions of voxels associated with various materials. This step includes obtaining and storing in data structures 327 conversion data 331 that indicates values for parameters that convert proton exposure to proton energy dose and acoustic pressure based on values at voxels in the medical imagery. In various embodiments, this is accomplished using properties of various materials inside the subject, using one or more models or simulations, such as described in the example embodiments section. The region of interest includes all or most of a volume inside the subject between the source of a proton beam and a target for the proton beam's Bragg Peaks and a superficial contact area for a 2D ultrasound transducer array.

In step 403, a proton beam treatment plan is obtained. The plan indicates the power, position and orientation of one or more proton beams emitted from one or more proton sources in one or more pulses.

In step 405, a position of a 2D ultrasound array outside the subject but close to the region of interest is proposed or otherwise specified. Also specified is the number and relative positions of the ultrasound transducers in the array.

In step 407, a training set is generated. The training set includes multiple instances. Each instance, as depicted in FIG. 3C, is based on the region of interest in the 3D medical imagery 330 with random alteration of the location and types of materials in the region of interest, and the treatment plan with random variations in the location, power and direction of the proton beams providing proton beam exposure and simulated proton energy dose 332 and simulated acoustic pressure 334 generated based on the conversion data 331, and propagation of acoustic waves 336 through the region of interest based on the material at each voxel to the 2D ultrasound array 338 based on the materials in the region of interest with random measurement noise and bias. Thus, each instance includes simulated proton dose delivered to a similar region of interest inside a second subject and simulated pressure generation from that simulated dose based on the conversion data and a similar 3D medical image and simulated acoustic transmission from the similar region of interest to a similar two-dimensional ultrasound transducer array similarly disposed.

In step 409, one or more neural networks are trained by using simulated signal at 2D ultrasound array 338 and varied treatment plan providing a proton exposure with simulated proton dose 332 (and optionally simulated 3D acoustic pressure 334) for each instance of most instances from the training set. In some embodiments, this includes simultaneously training two or more neural networks 366 and 376 that separately refine pressure and dose distributions, respectively, when approximate distributions are input. In some embodiments the one or more neural networks include one or more neural networks using conventional U-Net architecture. In some embodiments the neural networks advantageously include one or more modified U-Net architectures, such as modified to include 3D convolution, 3D downsampling, 3D up-sampling, dropout layers and batch normalization, alone or in some combination.

In step 411, the trained one or more neural networks are validated with training set data not used during training in step 409.

Once validation in step 411 indicates performance is satisfactory, then in step 413 the validated one or more neural networks are installed as neural network 328 in the dose detection module 326. Thus, the dose detection module includes a neural network trained on a plurality of training set instances. The training process then ends.

In some embodiments, the neural networks 328 are trained separately for each subject and treatment plan, so that the training process 400 is started hours or days before the treatment to develop the training set and train the neural networks to use during proton beam therapy of that particular subject for real-time proton energy dose detection. In other embodiments, neural networks 328 for a class of treatments for similar subjects and similar treatment plans and similar disposition of a similar 2D ultrasound transducer array are developed and repeatedly used for all patient treatments that fall into that class.

1.3. Method for Real-Time Proton Beam Dose Detection

Figure 5:
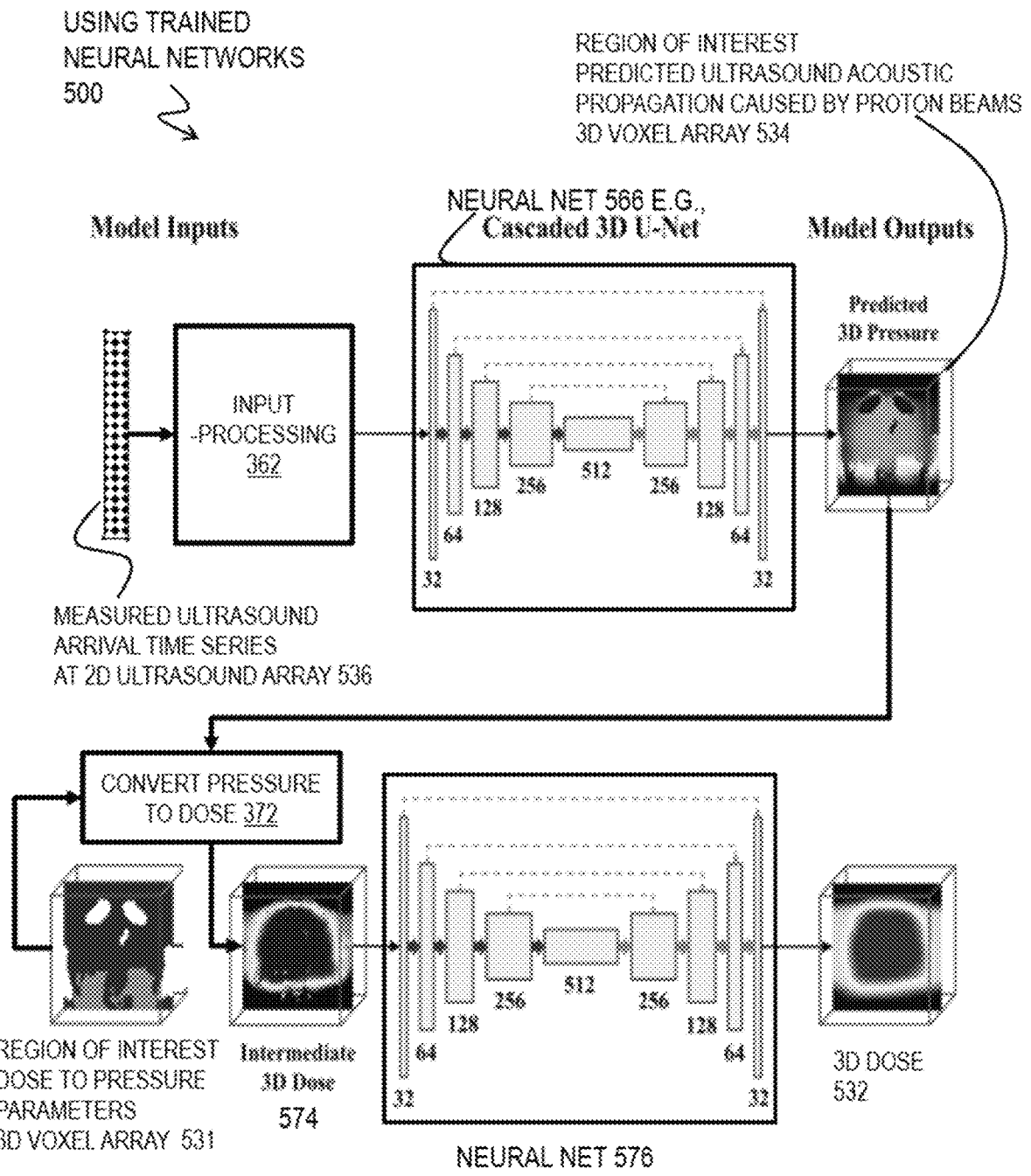
FIG. 5 is a block diagram that illustrates an example of a process using the trained deep-learning components in the dose detection module, according to an embodiment.

FIG. 5 is a block diagram that illustrates examples of a process 500 using the trained deep-learning components 328 in the dose detection module 326, according to an embodiment. In this embodiment, the input is newly measured ultrasound arrival time series at the 2D US array for a subject who is a patient undergoing proton beam therapy treatment. The input processing module 362 conditions the US RF signal output for input to trained neural network 566 (neural network 366 after training), including any use of a time reversal (TR) algorithm as described in more detail below. The trained neural network 566 outputs a corrected 3D pressure map for the ROI inside the patient that more closely matched the ground truth in the training set. The module 372 combines the output from trained neural network 566 with the dose-to-pressure parameter values 531 in the ROI for the patient undergoing therapy to produce an initial dose map 574. The initial dose map 574 is input to trained neural network 576 (neural network 376 after training) to output a refined or enhanced 3D dose map 532, equivalent to 3D dose data structure 329, which more closely matched the ground truth in the training set.

FIG. 6 is a flow diagram that illustrates an example of a method for using the trained the deep-learning components of the system of FIG. 3A to provide real-time detection of 3D dose delivered by proton beam therapy, according to an embodiment.

In step 651, a 3D medical scan is obtained for the next subject. In some embodiments, this step includes operating the medical scanner with the subject in view of the scanner and storing the result in data structures 327. In some embodiments, this step merely involves retrieving a previously collected 3D medical scan for the subject from a computer-readable medium, such as data structures 327. In some embodiments, step 651 includes segmenting the 3D medical image into different materials, and storing for subsequent retrieval conversion data that indicates values for parameters that convert proton exposure to proton energy dose and acoustic pressure based on values for those different materials at voxels in the segmented medical imagery. In some embodiments, the conversion parameter values for the different materials is already known and stored in one or more data structures 327 for retrieval.

In step 653, a proton beam treatment plan for next subject is obtained, which plan is similar to proton beam treatment plan used to train neural network. If a substantially different plan is used, e.g., with a target outside the region of interest, then a different trained neural network 328 should be used in the dose detection module 326. In some embodiments, the treatment plan is stored in data structures 327.

In step 655, a 2D ultrasound array is positioned relative to region of interest, which array and positioning is similar to position of 2D ultrasound array used to train neural network. If a substantially different array or positioning is used, e.g., nearer to a different region of interest or with more or fewer ultrasound transducers, then a different trained neural network 328 should be used in the dose detection module 326. In some respects, the use of a different array is less problematic than the use of a different propagating region of interest, because a TR algorithm may be relatively successful in determining from any array of ultrasound transducers the originating 3D pressure field that is input to the neural network 366 used in some embodiments.

In step 657, the one or more proton beam sources are operated to administer at least one pulse of the treatment plan. This exposes materials inside the region of interest of the subject to be exposed to a proton beam which causes proton energy to be deposited as a dose which causes thermal expansion with generates a pressure that propagates as ultrasound waves to any ultrasound transducers in contact with a surface of the subject.

In step 659, ultrasound arrival time series is measured at 2D ultrasound array 322. Thus, step 659 includes receiving a real-time signal that indicates ultrasound pressure received at a two-dimensional ultrasound transducer array disposed outside the first subject in contact with the subject close to the first region of interest. In some embodiments, step 659 includes storing the time series data, also called the RF signal, in data structures 327.

In step 661, measured ultrasound arrival time series data is input into dose detection module 326 with one or more trained neural networks 328 to output 3D dose map 329 for the region of interest in the subject. Such a 2D array preserves wave phase information that can be used to determine the direction of waves arriving at different points along the array. So, in some embodiments, the wave direction can be propagated backward in time to identify the source location and pressure of each arriving wave. In some embodiments, step 661 includes running the TR algorithm or incremental TR algorithm as module 364 to identify a first guess 3D pressure field. The 2D time series, or first guess 3D pressure (output by module 364 using the TR algorithm or an additional neural network using similar U-Net architectures as depicted in FIG. 3B), is input into a neural network 328, such as neural network 566, to output a corrected or enhanced 3D pressure map 534 or a corrected or enhanced 3D proton energy dose map 329, 532. In some embodiments, step 661 includes receiving a corrected 3D pressure map output by trained neural network 566 as input to trained neural network 576 that outputs a corrected or enhanced 3D proton energy dose map 329, 532. Thus, step 661 includes determining a real-time 3D dose delivered in the first region of interest inside the first subject by inputting the real-time signal into a dose detection module that includes a neural network trained on a plurality of training set instances.

In step 663, the proton beam source is operated based, at least in part, on 3D dose map 329, 532. For example, if the detected dose exceeds the therapy plan at the target or exceeds some safe threshold outside the target, then the proton beam source is turned off. Or, for example, if, after a pulse, the detected dose delivered to the target is below the plan and the detected dose delivered outside the target is below the safe threshold, then the proton beam source is operated to administer another proton beam pulse to complete the therapy.

In step 665, it is determined whether there is another treatment pulse to administer to the current subject. If so control passes back to step 657 and following steps. If not control passes to step 667. In step 667, it is determined whether there is another subject to treat. If so control passes back to step 651 and following steps. If not, the process ends.

Proton-acoustic imaging is a promising technique to achieve real-time dose verification to reduce the delivery uncertainties of proton therapy. Although the matrix array-based ultrasound reconstruction enables real-time 3D imaging of the target, it inevitably introduces distortions to the images due to its limited-angle views. In this study, we proposed a deep learning-based method to restore volumetric pressure and dose information from the limited-view acquisition of a matrix array. Our study demonstrated the effectiveness and efficiency of the proposed deep cascaded CNN model in predicting high-quality pressure maps using the pressure maps reconstructed from RF signals acquired by a matrix array and in deriving precise 3D dose maps from the predicted pressure maps.

The proposed method can provide a valuable tool for the online dose verification of prostate proton therapy during the treatment delivery. The transperineal ultrasound matrix array is convenient to deploy in the current RT workflow and has minimal impact on the treatment beam planning. During the treatment, radiation-induced RF signals can be acquired by the ultrasound array and used to reconstruct pressure maps, from which dose deposition maps are derived for dose verification. In this study, we focused on validating the feasibility of the proposed method in generating the 3D accumulated fractional dose for intrafraction treatment verification, which is crucial for daily treatment assessment and adaptive therapy in the clinical RT workflow. In the future, we would like to further investigate the capabilities of the method for verifying the dose delivered by individual proton pencil beams for intrafraction treatment verification, which can be valuable for minimizing dose deviations caused by intrafraction variations.

In this study, since the reconstructed pressure map is used as the input of the pressure map prediction model, the quality of the input reconstructed map directly affects the output of the prediction model. The iterative TR algorithm was used for the initial pressure map reconstruction since it achieved superior image quality compared to the TR algorithm. Compared to TR, despite little improvements in correcting distortions, iterative TR reconstructs pressures with higher SNR, which gives us a better starting image and thus leads to a better result after deep learning prediction. Similar image quality improvement has also been observed in our previous study 34. In future studies, advanced data-preprocess techniques can be employed to further improve the RF signal quality and/or input image quality, which can further improve the performance of our proposed method.

Besides the dose verification, the proposed method is potentially feasible for the 3D ultrasound image reconstruction using a matrix array, which suffers the same limited-view acquisition issue as this study.

Furthermore, the system and method can use onboard CBCT to derive the onboard anatomy. Although the image quality of CBCT is in general inferior to the CT, numerous methods have been developed to enhance CBCT image quality to be comparable to CT. Thus, the dose coefficient maps can potentially be derived from the onboard fractional CBCT images. Still further, the influence of air can be minimized by adjusting ultrasound array position and orientation, drinking water to fill the bladder, and filling rectum balloons.

The proposed deep cascaded CNN demonstrated the effectiveness and efficiency in substantially enhancing the image quality of the radiation-induced pressures acquired from a limited-view matrix array, as well as in deriving 3D precise quantitative dose deposition maps for in-vivo proton therapy dose verification. Besides, the proposed method presented a general workflow for enhancing limited-view image reconstruction, which is potentially applicable for matrix array-based 3D ultrasound imaging for applications in radiology and radiation oncology.

2. EXAMPLE EMBODIMENTS

An example embodiment has been built, demonstrated and evaluated for real-time detection of proton energy dose delivered to a prostate tumor in a human male patient as the subject. In the following description the term "RF signal" is used to refer to the electronic output from the 2D ultrasound transducer array.

2.1. Principles of Proton Beam Exposure Conversion to Dose and Pressure

Principles of proton-acoustic signal generation and propagation have been widely investigated and discussed in previous works [42, 43]. In brief, a proton deposits energy when traveling through tissues, which causes tissue temperature to rise and generates acoustic signals. Under the assumptions of thermal confinement, the process can be modeled as given in Equation 1.

$$\left(\nabla^2 - \frac{1}{c^2}\frac{\partial^2}{\partial t^2}\right)p(\vec{r},\,t) = -\frac{\beta\rho}{C_p}\frac{\partial D(\vec{r},\,t)}{\partial t} \tag{1}$$

where $p(\vec{r},\,t)$ denotes the acoustic pressure at location $\vec{r}$ and time t, c is the speed of sound, $\beta$ is the thermal expansion coefficient, $\rho$ is the density of the medium, $C_p$ denotes the medium's heat capacity at a constant pressure, and $D(\vec{r},\,t)$ is the dose deposition per unit time.

The amplitude of the proton-induced acoustic signal is proportional to the proton dose deposition per unit time in tissue when both thermal confinement and stress confinement are satisfied [44]. Therefore, for each proton pulse, the relationship between the initial pressure $p_{0\delta}(\vec{r})$ and the dose deposition rate $D_\delta(\vec{r})$ can be expressed as in Equation 2.

$$p_{0\delta}(\vec{r}) = \Gamma D_\delta(\vec{r})\rho \tag{2}$$

where $\Gamma = c^2\beta/C_p$ is the Grüneisen parameter, which describes the thermodynamic property of material, $D_\delta(\vec{r})$ is the dose deposition for each proton pencil beam, and p is the density of the material.

In the example embodiment, the fractional dose, $D(\vec{r})$ is to be verified, which dose is the sum of all the individual proton pencil beam dose depositions, as expressed in Equation 3.

$$D(\vec{r}) = \sum D_\delta(\vec{r}) \tag{3}$$

Then the corresponding initial pressure $p_0(\vec{r})$ can be expressed as in Equation 4.

$$p_0(\vec{r}) = \Gamma D(\vec{r})\rho \tag{4}$$

With the initial pressure map $p_0(\vec{r})$, based on Eq.1, the acoustic wave propagation can be solved as given in Equation 5.

$$p(\vec{r}, t) = \frac{\Gamma\rho}{4\pi c}\frac{\partial}{\partial t}\left(\frac{1}{ct}\int_{S(\vec{r},t)} D(\vec{r}', t)dS'(t)\right) \tag{5}$$

where S'(t) denotes a spherical surface that all points on the surface satisfy $|\vec{r} - \vec{r}'| = ct$.

Let $x_1 \in R^{I \times J \times K}$ be the real-valued limited-angle reconstructed pressure map with dimension I×J×K voxels, and $y_1 \in R^{I \times J \times K}$ be the corresponding ground truth pressure map, and $Y_2 \in R^{I \times J \times K}$ be the corresponding ground truth dose map. According to the above principles, the aimed task can be formulated as finding a pressure restoring pattern $f_1$ between the limited-angle reconstructed pressure map $x_1$ and the ground truth pressure map $y_1$, and a dose correction pattern $f_2$ between the intermediate dose map $$x_2 = \left(\frac{f_1(x_1)}{\rho \times \Gamma}\right)$$

(according to Eq. 4) and the ground truth dose map $Y_2$ so that the solution is expressed as given in Equation 6

$$\underset{f_1, f_2}{\text{argmin}}(\lambda_1 \overbrace{\|f_1(x_1) - y_1\|_2^2}^{\text{pressure restoration}} + \lambda_2 \overbrace{\|f_2(x_2) - y_2\|_2^2}^{\text{dose correction}}) \tag{6}$$

where ρ denotes the tissue density, Γ denotes the Grüneisen parameters defined in Eq. 2, $\lambda_1$ and $\lambda_2$ are the weighting factors for the pressure loss and the dose loss, respectively.

2.2. Use of Paired Neural Network Models

Two deep-learning models are cascaded and work jointly for optimized end-to-end performance. For each model, the multi-scale U-Net architecture is used. Based on the original U-Net [46], as described above, several major changes were made. First, in order to restore volumetric information from the TR-based pressures, 3D convolutional layers were adopted instead of 2D convolutional layers. Second, intensity distribution varies from sample to sample due to the anatomy and dose value changes. To standardize the inputs to each layer, batch normalization layers were added after convolutional layers. This technique has been widely discussed to be helpful in stabilizing and accelerating the training process with higher learning rates. Third, limited-view reconstruction is severely ill-conditioned. To avoid overfitting, dropout layers were used in the bottom of the U shape. By randomly enabling the feature connections, dropout layers result in varied network architecture during the training process, which potentially helps improve the network robustness and reduce overfitting. More details about the U-shape network in this study were shown above with reference to FIG. 3B.

To validate the effectiveness of the proposed method in pressure reconstruction and dose verification, the paired model's performance was evaluated using the proton prostate patient data.

2.3. Example Modified U-Net Architecture

In this embodiment, referring to FIG. 3B, the input layer 381 is a 3D image. The input layer may have been provided, in some embodiments, by an input processing module that denoises, and/or resamples, and reconstructs RF signals into a 3D spatial image. This input image is considered one channel of information as indicated by the value 1 depicted below the input layer 381. The input data dimension is indicated by the height of the line of the first channel. In the illustrated embodiment, each data dimension is halved at each of 4 sets of contractions to gain an increasing feature inception field.

The input layer is then processed, in this embodiment, by a convolution block which contains a 3D convolutional layer, a batch normalization (BN) layer, and a RELU activation function. The 3D convolutional layer contains multiple 3D kernels (the number of kernel is indicated by the value depicted below each line, and the size of kernel is indicated in the legend). Batch normalization is a method used to make training of artificial neural networks faster and more stable through normalization of the layers' inputs by re-centering and re-scaling. The activation function is used to introduce non-linearity to the model representation. The convolutional layer in the first convolution block contains 32 3D convolution kernel of size 3*3*3, generating 32 channels of information from the input image. A second convolution block is followed to generate 32 new channels of information from the output of the previous convolution block. But, in other embodiments different kernel numbers (e.g. 16) and size (e.g. 5*5*5) and different activation functions can be used.

Furthermore, in this example embodiment, the 32 channels of full size/resolution features output by the second convolution block are then contracted by a max pooling layer followed by another convolution block. In the illustrated embodiment, the max pooling is a 3D pool of 2×2×2 (i.e., a cube of 2 voxels by 2 voxels by 2 voxels is replaced by a single voxel holding the maximum value among those 8 values); but, in other embodiments a different pooling size (e.g., 3×3×3) or other method of producing the pooled value (e.g., averaging or minimum value or convolution with a stride of ≥2) may be used. Another two convolution blocks with doubled kernel number (64) are used to generate advanced features from the contracted features.

2.4. Training with Prostate Data

The proton-acoustic simulation workflow in this study is as shown above with reference to FIG. 3C and FIG. 3D but here in the specific example of CT prostate data. For each patient, CT images and the corresponding treatment plans were anonymized and collected. Dose map on each scan was calculated using commercial software, the RayStation (Ray-Search Laboratories, Stockholm/Sweden), and normalized to the maximum dose. The pressure map was calculated by multiplying the deposited dose, tissue density, and the Grüneisen parameter derived from the CT images. Generation and propagation of the proton-acoustic signals were simulated using the open-source k-wave toolbox [47]. A 2D matrix ultrasound array was simulated to receive acoustic signals during dose delivery. It was placed right below the prostate and near the perineum, with a 30° tilt relative to the patient superior-inferior direction to get a better acoustic window by avoiding the pelvic bones. In this embodiment, the first deep-learning model has input with 3D pressure reconstructed from the measurements at the 2D array. An initial 3D pressure distribution within a volume of size 12 cm×12 cm×14 cm above the matrix array was reconstructed in module 364 using the iterative TR algorithm (10 iterations), and was fed into the proposed first deep-learning model for quality enhancement and into the second deep-learning model for 3D dose map generation. More details of the proton-acoustic simulation are discussed as follows.

Data of 81 patients who have prostate cancers and underwent proton therapy in inventors' institutions were anonymized and collected for this study under an IRB protocol. For each patient, the planning CT scan, the clinical treatment plan, and up to 8 CT-quality assurance (CT-QA) scans were collected. The enrolled treatment plans have two opposite lateral beams delivering all prescribed doses to the prostate. QA scans were rigidly registered to the planning CT scan. Dose maps were calculated using a commercial software, the RayStation (RaySearch Laboratories, Stockholm/Sweden), and were normalized to the maximum dose.

In this embodiment, the CT volume was segmented into four kinds of materials, including air, fat, soft tissue, and bone, based on HU value thresholding. Air was overwritten to water to avoid acoustic impedance mismatch [48]. FIG. 7 is a table that illustrates an example list of values for parameters that convert proton dose to acoustic pressure based on intensity values at voxels of a 3D CT scan, according to an embodiment. The tissue-specific parameters used in this simulation are shown in the Table [49,50] of FIG. 7. In these example the region of interest is the vicinity of a prostate and the treatment is to dose a prostate tumor.

All the acoustic simulation was performed using the open-source k-wave toolbox 47 on Matlab (R2019b). The initial pressure maps (P0) were calculated based on the dose maps, the patient CT segmentation, and the tissue acoustic properties (shown in FIG. 7) according to Eq (3).

A planar ultrasound transducer array with 64×64 transducer elements was placed near the perineum area. The total size of the planar array is 8 cm×8 cm, which is large enough to cover the whole prostate area. To simulate realistic acquisitions, the central frequency of the transducer element was set to 500 kHz with 100% bandwidth and a sampling rate of 5 MHz. Tissue heterogeneity and attenuation (shown in FIG. 7) were considered during the simulation of the acoustic signal propagation. A Gaussian white noise (10 deciBels, dB, signal-to-noise ratio, SNR) was added to the acquired RF signals.

To balance between the image resolution and memory consumption, all the volume data were resampled to 1.25 mm×1.25 mm×1.25 mm. Thus, the grid size was set to 96×96×112. In addition, a 6-pixel perfectly matched layer (PML) was adopted in the simulation.

The pressure maps, which were used as the input of the proposed first DC-CNN, were reconstructed from the RF signals acquired by the matrix array using the TR algorithm

[45] in the k-wave toolbox. Compared to the conventional universal back-projection (UBP) algorithm [51], TR further considers the tissue heterogeneity, reconstructing more accurate results. In this study, CT-segmented structure maps were used in the TR reconstruction to account for the heterogeneous tissue acoustic properties.

To further improve the model input quality, an iterative TR algorithm was used for the pressure reconstruction. In each iteration, RF signal detection was calculated based on the reconstructed pressure map, and was compared to the real acquired RF signals. The RF signal differences were back-projected to reconstruct a residual pressure which was added to the current pressure to update the pressure map. The iteration was ended by either reaching the maximum iteration number of 10 or meeting the stopping criteria that the RF signal difference was less than 10%.

The proposed model was trained on a dataset containing 204 samples from 69 patients. 10% of the samples in the training dataset were used as validation data to monitor the training process and determine the best checkpoint.

In the training process, the TR-reconstructed limited-angle pressure maps and dose coefficient maps were used as inputs to the proposed model, as demonstrated in FIG. 3D. Model weights were optimized by minimizing the mean squared error (MSE) between the predicted and ground truth pressure maps combined with the MSE between the predicted and ground truth dose maps. The loss weights in Equation 6 were empirically set to $2\times10^{-6}$ and 1 for the pressure loss and the dose loss, respectively, according to the dynamic range of their values. The optimizer was set to "Adam" [52]. The learning rate was set to 0.001 and was gradually reduced to 0.0001. The batch size was set to 1 due to memory limitation.

2.5. Performance

The proposed model was tested on 26 samples from another 12 patients. Dose calculation and acoustic simulation followed the process described with reference to FIG. 5. For each testing case, initial pressure map was reconstructed from the RF signals using the iterative TR algorithm and was then fed into the trained model to generate enhanced pressure maps and dose maps, which were compared to the corresponding ground truth for evaluation. The pressure map output was then used with properties of the segmented CT scan to produce an initial dose map that was input to the second trained deep-learning model.

The enhanced pressure and dose maps were compared to the corresponding ground truth maps both qualitatively and quantitatively using root mean squared errors (RMSE). To further validate the performance of the proposed method in dose verification, the enhanced dose maps were evaluated using the isodose line Dice coefficient and the gamma index.

The Dice coefficient, which is also referred to as the overlap index, is a widely used metric in validating segmentation accuracy. In this study, the isodose lines (including 10%, 25%, 50%, 75%, and 90%) from dose maps were extracted and the Dice coefficients of the areas within isodose lines were calculated between the enhanced and ground truth dose maps.

The gamma index is used to evaluate the coincidence between the enhanced and the ground truth dose maps by calculating both the dose difference and the distance difference. In this study, the global gamma index analysis was performed with 3%/3 mm, 2%/3 mm, 3%/5 mm and 2%/5 mm thresholds.

Figure 8A:
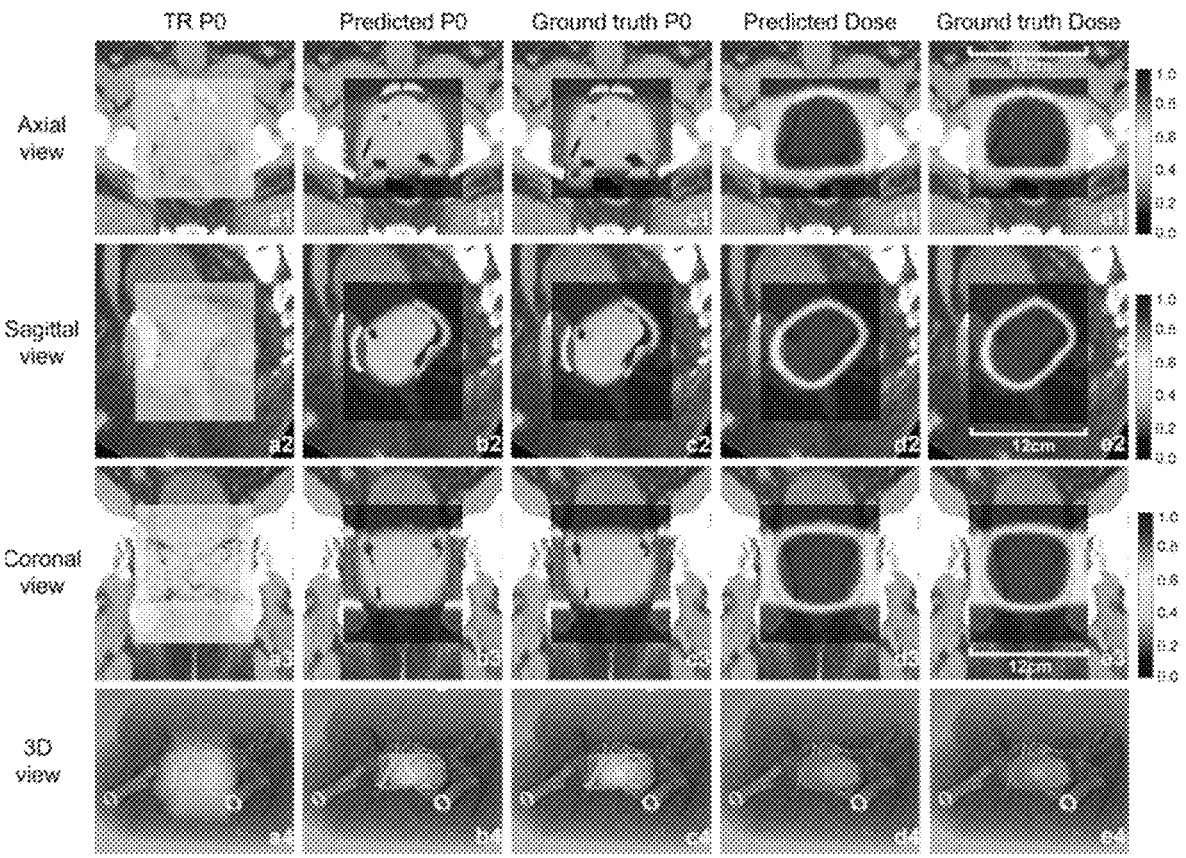
FIG. 8A is a so-called heat map comparing examples of outputs from the trained deep-learning components to "ground truth," according to an example embodiment.

FIG. 8A is a so-called heat map comparing examples of outputs from the trained deep-learning components to "ground truth," according to an example embodiment. Representative slices of the pressure and dose maps. (a) are the pressure maps (P0) reconstructed using the iterative time-reversal (TR) algorithm. (b) are the pressure maps enhanced by the proposed method. (c) are the ground truth pressure maps. (d) are the dose maps predicted by the proposed method. (e) are the ground truth dose maps. Thus, FIG. 8A shows a representative case in different slices and the 3D views. Due to the limited view of the ultrasound matrix array, pressures reconstructed by the iterative TR algorithm showed severe distortions, in which structures can hardly be distinguished from the artifacts. Our first deep-learning model effectively removed artifacts and corrected distortions, considerably improving the pressure map quality with accurate and clear structures and edges. Compared to the ground truth pressure maps, first deep-learning model restored most of the volumetric information precisely. And the predicted dose maps based on the predicted pressures agreed very well with the ground truth dose maps.

FIG. 8B is a table showing example of good performance (small root mean square error, RMSE) between ground truth and outputs from the trained deep-learning components of the system of FIG. 3A, according to an example embodiment. Table 2 of FIG. 8B shows the quantitative results of the predicted pressure and dose maps of our proposed method. Metric values are calculated from all the 26 cases from 12 testing patients. Both the predicted pressure maps and the dose maps showed low-intensity errors compared to the ground truth. The predicted dose maps showed a high similarity of the isodose lines compared with the ground truth, as indicated by the isodose line Dice coefficients. Results also showed a high agreement between the predicted and the ground truth 3D dose maps, as indicated by the high gamma index. Quantitative results further confirmed the effectiveness of the proposed method.

The proposed cascaded deep learning model was implemented using the Keras framework with Tensorflow backend. The model training and testing were performed on a computer equipped with a CPU of Intel Xeon and 32 GB memory and a GPU of NVIDIA Titan RTX (24 GB memory). The pressure enhancement and dose prediction with the proposed method are fully automatic, which takes about 0.22 second in total, easily satisfying the real-time definition.

3. COMPUTATIONAL HARDWARE OVERVIEW

FIG. 9 is a block diagram that illustrates a computer system 900 upon which an embodiment of the invention may be implemented. Computer system 900 includes a communication mechanism such as a bus 910 for passing information between other internal and external components of the computer system 900. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 900, or a portion thereof, constitutes a means for performing one or more steps of one or more methods described herein.

A sequence of binary digits constitutes digital data that is used to represent a number or code for a character. A bus 910 includes many parallel conductors of information so that information is transferred quickly among devices coupled to the bus 910. One or more processors 902 for processing information are coupled with the bus 910. A processor 902 performs a set of operations on information. The set of operations include bringing information in from the bus 910 and placing information on the bus 910. The set of operations also typically include comparing two or more units of information, shifting positions of units of information, and combining two or more units of information, such as by addition or multiplication. A sequence of operations to be executed by the processor 902 constitutes computer instructions.

Computer system 900 also includes a memory 904 coupled to bus 910. The memory 904, such as a random access memory (RAM) or other dynamic storage device, stores information including computer instructions. Dynamic memory allows information stored therein to be changed by the computer system 900. RAM allows a unit of information stored at a location called a memory address to be stored and retrieved independently of information at neighboring addresses. The memory 904 is also used by the processor 902 to store temporary values during execution of computer instructions. The computer system 900 also includes a read only memory (ROM) 906 or other static storage device coupled to the bus 910 for storing static information, including instructions, that is not changed by the computer system 900. Also coupled to bus 910 is a non-volatile (persistent) storage device 908, such as a magnetic disk or optical disk, for storing information, including instructions, that persists even when the computer system 900 is turned off or otherwise loses power.

Information, including instructions, is provided to the bus 910 for use by the processor from an external input device 912, such as a keyboard containing alphanumeric keys operated by a human user, or a sensor. A sensor detects conditions in its vicinity and transforms those detections into signals compatible with the signals used to represent information in computer system 900. Other external devices coupled to bus 910, used primarily for interacting with humans, include a display device 914, such as a cathode ray tube (CRT) or a liquid crystal display (LCD), for presenting images, and a pointing device 916, such as a mouse or a trackball or cursor direction keys, for controlling a position of a small cursor image presented on the display 914 and issuing commands associated with graphical elements presented on the display 914.

In the illustrated embodiment, special purpose hardware, such as an application specific integrated circuit (IC) 920, is coupled to bus 910. The special purpose hardware is configured to perform operations not performed by processor 902 quickly enough for special purposes. Examples of application specific ICs include graphics accelerator cards for generating images for display 914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 900 also includes one or more instances of a communications interface 970 coupled to bus 910. Communication interface 970 provides a two-way communication coupling to a variety of external devices that operate with their own processors, such as printers, scanners and external disks. In general the coupling is with a network link 978 that is connected to a local network 980 to which a variety of external devices with their own processors are connected. For example, communication interface 970 may be a parallel port or a serial port or a universal serial bus (USB) port on a personal computer. In some embodiments, communications interface 970 is an integrated services digital network (ISDN) card or a digital subscriber line (DSL) card or a telephone modem that provides an information communication connection to a corresponding type of telephone line. In some embodiments, a communication interface 970 is a cable modem that converts signals on bus 910 into signals for a communication connection over a coaxial cable or into optical signals for a communication connection over a fiber optic cable. As another example, communications interface 970 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 970 sends and receives electrical, acoustic or electromagnetic signals, including infrared and optical signals, that carry information streams, such as digital data.

The term computer-readable medium is used herein to refer to any medium that participates in providing information to processor 902, including instructions for execution. Such a medium may take many forms, including, but not limited to, non-volatile media, volatile media and transmission media. Non-volatile media include, for example, optical or magnetic disks, such as storage device 908. Volatile media include, for example, dynamic memory 904. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 902, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 902, except for carrier waves and other signals.

Logic encoded in one or more tangible media includes one or both of processor instructions on a computer-readable storage media and special purpose hardware, such as ASIC 920.

Network link 978 typically provides information communication through one or more networks to other devices that use or process the information. For example, network link 978 may provide a connection through local network 980 to a host computer 982 or to equipment 984 operated by an Internet Service Provider (ISP). ISP equipment 984 in turn provides data communication services through the public, world-wide packet-switching communication network of networks now commonly referred to as the Internet 990. A computer called a server 992 connected to the Internet provides a service in response to information received over the Internet. For example, server 992 provides information representing video data for presentation at display 914.

The invention is related to the use of computer system 900 for implementing the techniques described herein. According to one embodiment of the invention, those techniques are performed by computer system 900 in response to processor 902 executing one or more sequences of one or more instructions contained in memory 904. Such instructions, also called software and program code, may be read into memory 904 from another computer-readable medium such as storage device 908. Execution of the sequences of instructions contained in memory 904 causes processor 902 to perform the method steps described herein. In alternative embodiments, hardware, such as application specific integrated circuit 920, may be used in place of or in combination with software to implement the invention. Thus, embodiments of the invention are not limited to any specific combination of hardware and software.

The signals transmitted over network link 978 and other networks through communications interface 970, carry information to and from computer system 900. Computer system 900 can send and receive information, including program code, through the networks 980, 990 among others, through network link 978 and communications interface 970. In an example using the Internet 990, a server 992 transmits program code for a particular application, requested by a message sent from computer 900, through Internet 990, ISP equipment 984, local network 980 and communications interface 970. The received code may be executed by processor 902 as it is received, or may be stored in storage device 908 or other non-volatile storage for later execution, or both. In this manner, computer system 900 may obtain application program code in the form of a signal on a carrier wave.

Various forms of computer readable media may be involved in carrying one or more sequence of instructions or data or both to processor 902 for execution. For example, instructions and data may initially be carried on a magnetic disk of a remote computer such as host 982. The remote computer loads the instructions and data into its dynamic memory and sends the instructions and data over a telephone line using a modem. A modem local to the computer system 900 receives the instructions and data on a telephone line and uses an infra-red transmitter to convert the instructions and data to a signal on an infra-red a carrier wave serving as the network link 978. An infrared detector serving as communications interface 970 receives the instructions and data carried in the infrared signal and places information representing the instructions and data onto bus 910. Bus 910 carries the information to memory 904 from which processor 902 retrieves and executes the instructions using some of the data sent with the instructions. The instructions and data received in memory 904 may optionally be stored on storage device 908, either before or after execution by the processor 902.

FIG. 10 illustrates a chip set 1000 upon which an embodiment of the invention may be implemented. Chip set 1000 is programmed to perform one or more steps of a method described herein and includes, for instance, the processor and memory components described with respect to FIG. 9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1000, or a portion thereof, constitutes a means for performing one or more steps of a method described herein.

In one embodiment, the chip set 1000 includes a communication mechanism such as a bus 1001 for passing information among the components of the chip set 1000. A processor 1003 has connectivity to the bus 1001 to execute instructions and process information stored in, for example, a memory 1005. The processor 1003 may include one or more processing cores with each core configured to perform independently. A multi-core processor enables multiprocessing within a single physical package. Examples of a multi-core processor include two, four, eight, or greater numbers of processing cores. Alternatively or in addition, the processor 1003 may include one or more microprocessors configured in tandem via the bus 1001 to enable independent execution of instructions, pipelining, and multithreading. The processor 1003 may also be accompanied with one or more specialized components to perform certain processing functions and tasks such as one or more digital signal processors (DSP) 1007, or one or more application-specific integrated circuits (ASIC) 1009. A DSP 1007 typically is configured to process real-world signals (e.g., sound) in real time independently of the processor 1003. Similarly, an ASIC 1009 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1003 and accompanying components have connectivity to the memory 1005 via the bus 1001. The memory 1005 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1005 also stores the data associated with or generated by the execution of one or more steps of the methods described herein.

4. ALTERNATIVES, DEVIATIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

5. REFERENCES

All the references listed here are hereby incorporated by reference as if fully set forth herein except for terminology inconsistent with that used herein.

1. Lu H M, Mann G, Cascio E. Investigation of an implantable dosimeter for single-point water equivalent path length verification in proton therapy. Medical physics. 2010; 37(11):5858-5866.
2. Telsemeyer J, Jäkel O, Martišíková M. Quantitative carbon ion beam radiography and tomography with a flat-panel detector. Physics in Medicine & Biology. 2012; 57(23):7957.
3. Bentefour E H, Shikui T, Prieels D, Lu H-M. Effect of tissue heterogeneity on an in vivo range verification technique for proton therapy. Physics in Medicine & Biology. 2012; 57(17):5473.
4. Schneider U, Besserer J, Pemler P, et al. First proton radiography of an animal patient. Medical physics. 2004; 31(5):1046-1051.
5. Schneider U, Pedroni E, Hartmann M, Besserer J, Lomax T. Spatial resolution of proton tomography: methods, initial phase space and object thickness. Zeitschrift für Medizinische Physik. 2012; 22(2):100-108.
6. Penfold S, Rosenfeld A B, Schulte R, Schubert K. A more accurate reconstruction system matrix for quantitative proton computed tomography. Medical physics. 2009; 36(10):4511-4518.
7. Fiedler F, Priegnitz M, Juelich R, et al. In-beam PET measurements of biological half-lives of 12C irradiation induced β+-activity. Acta Oncologica. 2008; 47(6): 1077-1086.
8. Fiedler F, Shakirin G, Skowron J, et al. On the effectiveness of ion range determination from in-beam PET data. Physics in Medicine & Biology. 2010; 55(7): 1989.
9. Nishio T, Miyatake A, Ogino T, Nakagawa K, Saijo N, Esumi H. The development and clinical use of a beam ON-LINE PET system mounted on a rotating gantry port in proton therapy. International Journal of Radiation Oncology* Biology* Physics. 2010; 76(1):277-286.

10. Miyatake A, Nishio T, Ogino T, Saijo N, Esumi H, Uesaka M. Measurement and verification of positron emitter nuclei generated at each treatment site by target nuclear fragment reactions in proton therapy. Medical physics. 2010; 37(8):4445-4455.

11. Min C-H, Kim C H, Youn M-Y, Kim J-W. Prompt gamma measurements for locating the dose falloff region in the proton therapy. Applied physics letters. 2006; 89(18):183517.

12. Min C H, Lee H R, Kim C H, Lee S B. Development of array-type prompt gamma measurement system for in vivo range verification in proton therapy. Medical physics. 2012; 39(4):2100-2107.

13. Kormoll T, Fiedler F, Schöne S, Wustemann J, Zuber K, Enghardt W. A Compton imager for in-vivo dosimetry of proton beams—A design study. Nuclear Instruments and Methods in Physics Research Section A: Accelerators, Spectrometers, Detectors and Associated Equipment. 2011; 626:114-119.

14. Polf J, Peterson S, Ciangaru G, Gillin M, Beddar S. Prompt gamma-ray emission from biological tissues during proton irradiation: a preliminary study. Physics in Medicine & Biology. 2009; 54(3):731.

15. Draeger E, Mackin D, Peterson S, et al. 3D prompt gamma imaging for proton beam range verification. Physics in Medicine & Biology. 2018; 63(3):035019.

16. Parodi K, Paganetti H, Shih H A, et al. Patient study of in vivo verification of beam delivery and range, using positron emission tomography and computed tomography imaging after proton therapy. International Journal of Radiation Oncology* Biology* Physics. 2007; 68(3):920-934.

17. Polf J C, Barajas C A, Peterson S W, et al. Applications of machine learning to improve the clinical viability of Compton camera based in vivo range verification in proton radiotherapy. Frontiers in Physics. 2022:284.

18. Xie Y, Bentefour E H, Janssens G, et al. Prompt gamma imaging for in vivo range verification of pencil beam scanning proton therapy. International Journal of Radiation Oncology* Biology* Physics. 2017; 99(1):210-218.

19. Gensheimer M F, Yock T I, Liebsch N J, et al. In vivo proton beam range verification using spine MRI changes. International Journal of Radiation Oncology* Biology* Physics. 2010; 78(1):268-275.

20. Yuan Y, Andronesi O C, Bortfeld T R, et al. Feasibility study of in vivo MRI based dosimetric verification of proton end-of-range for liver cancer patients. Radiotherapy and Oncology. 2013; 106(3):378-382.

21. Ahmad M, Xiang L, Yousefi S, Xing L. Theoretical detection threshold of the proton-acoustic range verification technique. Medical physics. 2015; 42(10):5735-5744.

22. Jones K C, Vander Stappen F, Bawiec C R, et al. Experimental observation of acoustic emissions generated by a pulsed proton beam from a hospital-based clinical cyclotron. Medical physics. 2015; 42(12):7090-7097.

23. Assmann W, Kellnberger S, Reinhardt S, et al. Ionoacoustic characterization of the proton Bragg peak with submillimeter accuracy. Medical physics. 2015; 42(2):567-574.

24. Freijo C, Herraiz J L, Sanchez-Parcerisa D, Udias J M. Dictionary-based protoacoustic dose map imaging for proton range verification. Photoacoustics. 2021; 21:100240.

25. Yu Y, Li Z, Zhang D, Xing L, Peng H. Simulation studies of time reversal-based protoacoustic reconstruction for range and dose verification in proton therapy. Medical physics. 2019; 46(8):3649-3662.

26. Yao S, Hu Z, Zhang X, et al. Feasibility study of range verification based on proton-induced acoustic signals and recurrent neural network. Physics in Medicine & Biology. 2020; 65(21):215017.

27. Yao S, Hu Z, Xie Q, Yang Y, Peng H. Further investigation of 3D dose verification in proton therapy utilizing acoustic signal, wavelet decomposition and machine learning. Biomedical Physics & Engineering Express. 2021; 8(1):015008.

28. Yu J, Yoon H, Khalifa $Y_M$, Emelianov S Y. Design of a volumetric imaging sequence using a Vantage-256 ultrasound research platform multiplexed with a 1024-element fully sampled matrix array. IEEE transactions on ultrasonics, ferroelectrics, and frequency control. 2019; 67(2):248-257.

29. Wang M, Samant P, Wang S, et al. Toward in vivo dosimetry for prostate radiotherapy with a transperineal ultrasound array: A simulation study. IEEE transactions on radiation and plasma medical, sciences. 2020; 5(3):373-382.

30. Maier A, Syben C, Lasser T, Riess C. A gentle introduction to deep learning in medical image processing. Zeitschrift fUr Medizinische Physik. 2019; 29(2):86-101.

31. Litjens G, Kooi T, Bejnordi B E, et al. A survey on deep learning in medical image analysis. Medical image analysis. 2017; 42:60-88.

32. Zhang H-M, Dong B. A review on deep learning in medical image reconstruction. Journal of the Operations Research Society of China. 2020; 8(2):311-340.

33. Chen H, Zhang Y, Chen Y, et al. LEARN: Learned experts' assessment-based reconstruction network for sparse-data C T. IEEE transactions on medical imaging. 2018; 37(6):1333-1347.

34. Jiang Z, Chen Y, Zhang Y, Ge Y, Yin F-F, Ren L. Augmentation of CBCT reconstructed from undersampled projections using deep learning. IEEE transactions on medical imaging. 2019; 38(11):2705-2715.

35. Schlemper J, Caballero J, Hajnal J V, Price A N, Rueckert D. A deep cascade of convolutional neural networks for dynamic M R image reconstruction. IEEE transactions on Medical Imaging. 2017; 37(2):491-503.

36. Huang Y, Preuhs A, Lauritsch G, Manhart M, Huang X, Maier A. Data consistent artifact reduction for limited angle tomography with deep learning prior. Paper presented at: International workshop on machine learning for medical image reconstruction 2019.

37. Jiang Z, Yin F-F, Ge Y, Ren L. Enhancing digital tomosynthesis (DTS) for lung radiotherapy guidance using patient-specific deep learning model. Physics in Medicine & Biology. 2021; 66(3):035009.

38. Cheng A, Kim Y, Anas E M, et al. Deep learning image reconstruction method for limited-angle ultrasound tomography in prostate cancer. Paper presented at: Medical Imaging 2019: Ultrasonic Imaging and Tomography 2019.

39. Jiang Z, Yin F-F, Ge Y, Ren L. A multi-scale framework with unsupervised joint training of convolutional neural networks for pulmonary deformable image registration. Physics in Medicine & Biology. 2020; 65(1): 015011.

40. Yang Y, Hu Y, Zhang X, Wang S. Two-stage selective ensemble of CNN via deep tree training for medical image classification. IEEE Transactions on Cybernetics. 2021.

41. Tajbakhsh N, Jeyaseelan L, Li Q, Chiang J N, Wu Z, Ding X. Embracing imperfect datasets: A review of deep learning solutions for medical image segmentation. Medical Image Analysis. 2020; 63:101693.

42. Lascaud J, Dash P, Wieser H-P, et al. Investigating the accuracy of co-registered ionoacoustic and ultrasound images in pulsed proton beams. Physics in Medicine & Biology. 2021; 66(18):185007.

43. Forghani F, Mahl A, Patton T J, et al. Simulation of x-ray-induced acoustic imaging for absolute dosimetry: Accuracy of image reconstruction methods. Medical Physics. 2020; 47(3):1280-1290.

44. Hickling S, Xiang L, Jones K C, et al. Ionizing radiation-induced acoustics for radiotherapy and diagnostic radiology applications. Medical physics. 2018; 45(7):e707-e721.

45. Hristova Y, Kuchment P, Nguyen L. Reconstruction and time reversal in thermoacoustic tomography in acoustically homogeneous and inhomogeneous media. Inverse problems. 2008; 24(5):055006.

46. Ronneberger O, Fischer P, Brox T. U-net: Convolutional networks for biomedical image segmentation. Paper presented at: International Conference on Medical image computing and computer-assisted intervention 2015.

47. Treeby B E, Cox B T. k-Wave: MATLAB toolbox for the simulation and reconstruction of photoacoustic wave fields. Journal of biomedical optics. 2010; 15(2): 021314.

48. Jones K C, Nie W, Chu J C, et al. Acoustic-based proton range verification in heterogeneous tissue: simulation studies. Physics in Medicine & Biology. 2018; 63(2):025018.

49. Yao D-K, Zhang C, Maslov K I, Wang L V. Photoacoustic measurement of the GrUneisen parameter of tissue. Journal of biomedical optics. 2014; 19(1): 017007.

50. Prince J L, Links J M. Medical imaging signals and systems. Pearson Prentice Hall Upper Saddle River; 2006.

51. Xu M, Wang L V. Universal back-projection algorithm for photoacoustic computed tomography. Physical Review E. 2005; 71(1):016706.

52. Kingma D P, Ba J. Adam: A method for stochastic optimization. arXiv preprint arXiv:14126980. 2014.

53. Jiang Z, Zhang Z, Chang Y, Ge Y, Yin F-F, Ren L. Prior image-guided cone-beam computed tomography augmentation from under-sampled projections using a convolutional neural network. Quantitative imaging in medicine and surgery. 2021; 11(12):4767.

What is claimed is:

1. A method executed on a processor for real-time detection of dose delivered to tissue by a proton beam, wherein real-time indicates within ten seconds of actual occurrence, the method comprising:

retrieving conversion data that indicates values for parameters that convert proton exposure to proton energy dose and acoustic pressure based on values at voxels in medical imagery;

retrieving a 3D medical image of a first region of interest inside a first subject;

receiving a real-time signal that indicates ultrasound pressure received at a two-dimensional ultrasound transducer array disposed outside the first subject in contact with the subject close to the first region of interest; and determining a real-time 3D dose delivered in the first region of interest inside the first subject by inputting the real-time signal into a dose detection module that includes a neural network trained on a plurality of training set instances, each instance including simulated proton dose delivered to a similar region of interest inside a second subject and simulated pressure generation from that simulated dose based on the conversion data and a similar 3D medical image and simulated acoustic transmission from the similar region of interest to a similar two-dimensional ultrasound transducer array similarly disposed.

2. The method as recited in claim 1, wherein the neural network has a multi-scale U-net architecture modified to include a 3D convolution hidden layer.

3. The method as recited in claim 2, wherein the neural network includes a batch normalization hidden layer after the 3D convolution hidden layer.

4. The method as recited in claim 1, wherein the neural network has a multi-scale U-net architecture modified to include dropout hidden layer in a bottom of the U-net between contracting layers and expanding layers.

5. The method as recited in claim 1, wherein the 3D medical image of the subject and the similar 3D medical image in each instance is segmented into at least four kinds of materials, including air, fat, soft tissue, and bone, each with a different value for a parameter to convert proton dose to pressure.

6. The method as recited in claim 5, wherein a value for a parameter to convert proton dose to pressure in air is replaced with a value for the parameter to convert proton dose to pressure in water.

7. The method as recited in claim 1, wherein the 3D medical image of the subject and the similar 3D medical image in each instance is a computerized tomography 3D image segmented into at least four kinds of materials, including air, fat, soft tissue, and bone based on Hounsfield unit (HU) value thresholding, each with a different value for a parameter to convert proton dose to pressure.

8. The method as recited in claim 1, wherein the dose detection module includes a first neural network trained on the simulated pressure generation from the simulated dose as output and simulated acoustic transmission from the similar region of interest to a similar two-dimensional ultrasound transducer array as input.

9. The method as recited in claim 8, wherein the dose detection module includes a second neural network trained on the simulated proton dose as output and the simulated pressure generation from that simulated dose as input.

10. The method as recited in claim 1, wherein the dose detection module includes a first neural network trained on the simulated proton dose as output and the simulated pressure generation from that simulated dose as input.

11. The method as recited in claim 1, wherein the dose detection module includes a time-reversal (TR) algorithm that outputs 3D pressure based on acoustic transmission from the region of interest to the two-dimensional ultrasound transducer array using the real-time signal and the conversion data and the 3D medical image as input.

12. The method as recited in claim 11, wherein the dose detection module includes a first neural network trained on the simulated pressure generation from the simulated dose as output and 3D pressure from the TR algorithm as input.

13. The method as recited in claim 1, wherein the similar 3D medical image in every instance of the training set is identical to the 3D medical image of the first region of interest inside the first subject.

14. The method as recited in claim 1, wherein the simulated acoustic transmission from the similar region of interest to a similar two-dimensional ultrasound transducer array includes a different random measurement error in each different instance of the training set.

15. The method as recited in claim 1, wherein the simulated acoustic transmission from the similar region of interest to a similar two-dimensional ultrasound transducer array includes a different random measurement error in each different instance of the training set.

16. The method as recited in claim 1, wherein the simulated proton dose includes a different random spatial displacement in each different instance of the training set.

17. The method as recited in claim 1, wherein the two-dimensional ultrasound transducer array similarly disposed includes a different random spatial displacement in each different instance of the training set.

18. A non-transitory computer-readable medium carrying one or more sequences of instructions, wherein execution of the one or more sequences of instructions by one or more processors causes the one or more processors to perform the steps of:

retrieving conversion data that indicates values for parameters that convert proton dose to acoustic pressure based on values at voxels in medical imagery;

retrieving a 3D medical image of a first region of interest inside a first subject;

receiving a real-time signal that indicates ultrasound pressure received at a two-dimensional ultrasound transducer array disposed outside the first subject in contact with the subject close to the region of interest; and determining a real-time 3D dose delivered in the region of interest inside the subject by inputting the real-time signal into a dose detection module that includes a neural network trained on a plurality of training set instances, each instance including simulated proton dose delivered to a similar region of interest inside a second subject and simulated pressure generation from that simulated dose based on the conversion data and a similar 3D medical image and simulated acoustic transmission from the similar region of interest to a similar two-dimensional ultrasound transducer array similarly disposed.

19. An apparatus comprising:

at least one processor; and at least one computer-readable medium including one or more sequences of instructions and one or more data structures, the at least one computer-readable medium and the one or more sequences of instructions configured to, with the at least one processor, cause the apparatus to perform at least the following, retrieving, from the one or more data structures, conversion data that indicates values for parameters that convert proton dose to acoustic pressure based on values at voxels in medical imagery;

retrieving, from the one or more data structures, a 3D medical image of a first region of interest inside a first subject;

receiving a real-time signal that indicates ultrasound pressure received at a two-dimensional ultrasound transducer array disposed outside the first subject in contact with the subject close to the region of interest; and determining a real-time 3D dose delivered in the first region of interest inside the first subject by inputting the real-time signal into a dose detection module that includes a neural network trained on a plurality of training set instances, each instance including simulated proton dose delivered to a similar region of interest inside a second subject and simulated pressure generation from that simulated dose based on the conversion data and a similar 3D medical image and simulated acoustic transmission from the similar region of interest to a similar two-dimensional ultrasound transducer array similarly disposed.

20. A system for real-time detection of dose delivered to tissue by a proton beam, wherein real-time indicates within ten seconds of actual occurrence, the system comprising:

a two-dimensional ultrasound transducer array disposed outside a first subject in contact with the first subject close to a first region of interest inside the first subject;

a processor;

a computer-readable medium carrying one or more sequences of instructions and storing one or more data structures, wherein execution of the one or more sequences of instructions by the processor causes the processor to perform the steps of retrieving, from the data structure, conversion data that indicates values for parameters that convert proton dose to acoustic pressure based on values at voxels in medical imagery;

retrieving, from the data structure, a 3D medical image of the first region of interest inside the first subject;

receiving a real-time signal that indicates ultrasound pressure received at the two-dimensional ultrasound transducer array; and determining a real-time 3D dose delivered in the first region of interest inside the first subject by inputting the real-time signal into a dose detection module that includes a neural network trained on a plurality of training set instances, each instance including simulated proton dose delivered to a similar region of interest inside a second subject and simulated pressure generation from that simulated dose based on the conversion data and a similar 3D medical image and simulated acoustic transmission from the similar region of interest to a similar two-dimensional ultrasound transducer array similarly disposed.

* * * * *